US012655179B2

(12) United States Patent
Siegert et al.

(10) Patent No.: US 12,655,179 B2
(45) Date of Patent: Jun. 16, 2026

(54) SYNTHESIS OF AMANIN AND ITS DERIVATIVES

(71) Applicant: HEIDELBERG PHARMA RESEARCH GMBH, Ladenburg (DE)

(72) Inventors: Mary-Ann Siegert, Berlin (DE); Caroline Knittel, Berlin (DE); Roderich Süssmuth, Berlin (DE)

(73) Assignee: HEIDELBERG PHARMA RESEARCH GMBH, Ladenburg (DE)

( * ) Notice: Subject to any disclaimer, the term of this patent is extended or adjusted under 35 U.S.C. 154(b) by 971 days.

(21) Appl. No.: 17/785,574

(22) PCT Filed: Dec. 16, 2020

(86) PCT No.: PCT/EP2020/086416

§ 371 (c)(1),
(2) Date: Jun. 15, 2022

(87) PCT Pub. No.: WO2021/122744

PCT Pub. Date: Jun. 24, 2021

(65) Prior Publication Data

US 2023/0039142 A1 Feb. 9, 2023

(30) Foreign Application Priority Data

Dec. 16, 2019 (EP) .................................... 19216705

(51) Int. Cl.
*C07K 7/64* (2006.01)
*C07K 1/10* (2006.01)

(52) U.S. Cl.
CPC . *C07K 7/64* (2013.01); *C07K 1/10* (2013.01)

(58) Field of Classification Search
None
See application file for complete search history.

(56) References Cited

U.S. PATENT DOCUMENTS

| | | |
|---|---|---|
| 2021/0113707 A1 | 4/2021 | Zhu et al. |

FOREIGN PATENT DOCUMENTS

| | | |
|---|---|---|
| WO | WO 2017/046658 A1 | 3/2017 |
| WO | WO 2017/089607 A1 | 6/2017 |
| WO | WO 2019/030171 A1 | 2/2019 |
| WO | WO 2019/030173 A1 | 2/2019 |
| WO | WO 2019/047941 A1 | 3/2019 |

OTHER PUBLICATIONS

Zhao. ChemBioChem Communications, 2015, 16, 1420-1425 (Year: 2015).*

Lutz et al., "Total Synthesis of α- and β-Amanitin," *Angew. Chem. Int. Ed.*, 59(28): 11390-11393 (2020).

Matinkhoo et al., "Synthesis of the Death-Cap Mushroom Toxin α-Amanitin," *J. Am. Chem. Soc.*, 140(21): 6513-6517 (2018).

Siegert et al., "A Convergent Total Synthesis of the Death Cap Toxin α-Amanitin," *Angew. Chem. Int. Ed.*, 59(14): 5500-5504 (2020).

* cited by examiner

*Primary Examiner* — Noble E Jarrell

(74) *Attorney, Agent, or Firm* — McBee, Moore & Vanik IP, LLC

(57) ABSTRACT

The present invention relates to the chemical synthesis of amanin and its derivatives. The present invention also relates to intermediate products of the amanin synthesis.

17 Claims, 2 Drawing Sheets

1

2

3

4

5

6

7

8

SYNTHESIS OF AMANIN AND ITS DERIVATIVES

The present invention relates to the chemical synthesis of amanin and its derivatives. The present invention also relates to intermediate products of the amanin synthesis.

BACKGROUND OF THE INVENTION

The objective of the present invention is to provide means and methods to chemically synthesize amanin or derivatives thereof. This objective is attained by the subject-matter of the independent claims of the present specification.

SUMMARY OF THE INVENTION

A first aspect of the invention relates to a method for preparation of a compound of formula (I)

(I)

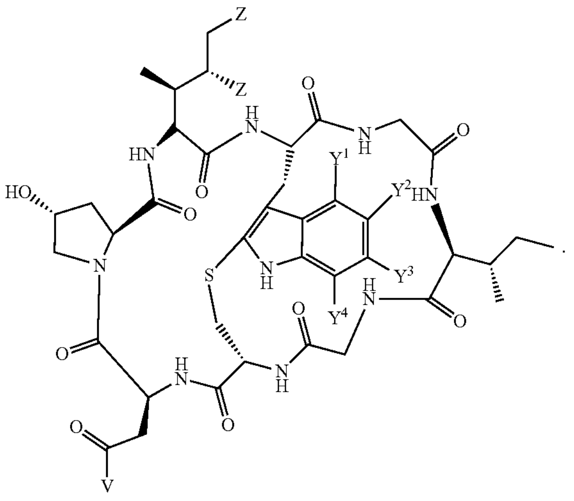

Other aspects relate to intermediate products of the amanin synthesis.

DETAILED DESCRIPTION OF THE INVENTION

Terms and Definitions

Figure 1:
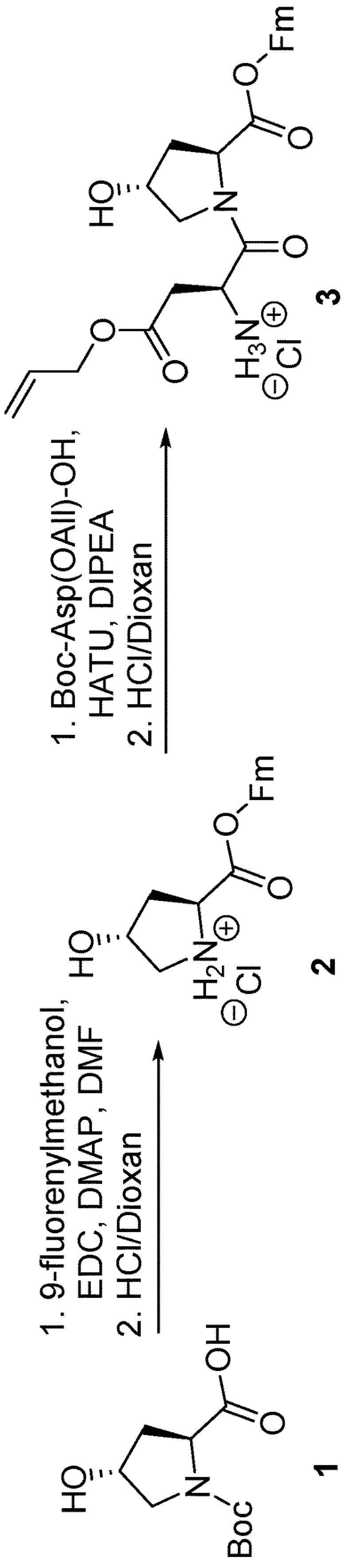
FIG. 1 Synthesis of the dipeptide building block H-Asp (OAll)-Hyp-OFm○HCl (3).

Amino acid sequences are given from amino to carboxyl terminus. Capital letters for sequence positions refer to L-amino acids in the one-letter code (Stryer, Biochemistry, 3$^{rd}$ ed. p. 21). Lower case letters for amino acid sequence positions refer to the corresponding D- or (2R)-amino acids.

The term AA in the context of the present specification relates to amino acid.

The term "protecting group" in the context of the present specification relates to a moiety covalently attached to a functional group (particularly the carboxylic acid moiety, the amino moiety or the hydroxyl moiety of the molecules discussed herein) that can be selectively attached to the functional group and selectively removed without affecting the integrity or chiral orientation of the carbon backbone of the molecule the protecting group is attached to, nor cleaving particular other protecting groups attached to other protecting groups attached to the molecule.

The term "deprotection agent" in the context of the present specification relates to an agent which is able to cleave a certain protecting group. The skilled person is able to select the deprotection agent according to the protecting group. The conditions under which the protecting group is cleavable constitute the deprotection agent, e.g. if the protecting group is cleavable under acidic conditions, then the deprotection agent is an acid.

The term "preactivated carboxylic group" in the context of the present specification relates to a carboxylic moiety being reacted into an active ester susceptible for the nucleophilic attack of an amine group in order to form a peptide bond.

The term "preactivated amino group" in the context of the present specification relates to an amino group being reacted into a N-trimethylsilyl amine with increased nucleophilicity to attack a carboxylic acid moiety in order to form a peptide bond.

A comprehensive review of modern protecting group chemistry, particularly as it pertains to the compounds disclosed herein, is available in Peter G. M. Wuts, Greene's Protective Groups in Organic Synthesis, 5th Edition, Wiley 2014.

U.S. Pat. No. 6,693,178 B2—"Protecting groups useful in the synthesis of polysaccharides, natural products, and combinatorial libraries" and US 20160024143 A1—"Deprotection method" are incorporated herein by reference.

Standard convention of organic chemistry, by which a non-designated position in a formula is deemed to be a saturated carbon, is followed herein.

A first aspect of the invention relates to a method for preparation of a compound of formula (I)

(I)

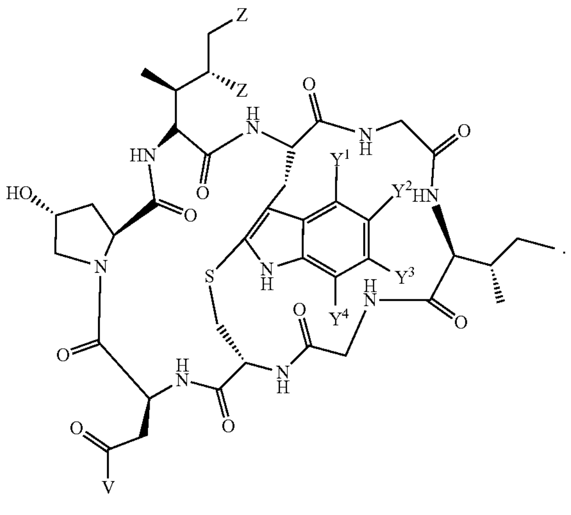

wherein a) a compound of formula (IIa)

(IIa)

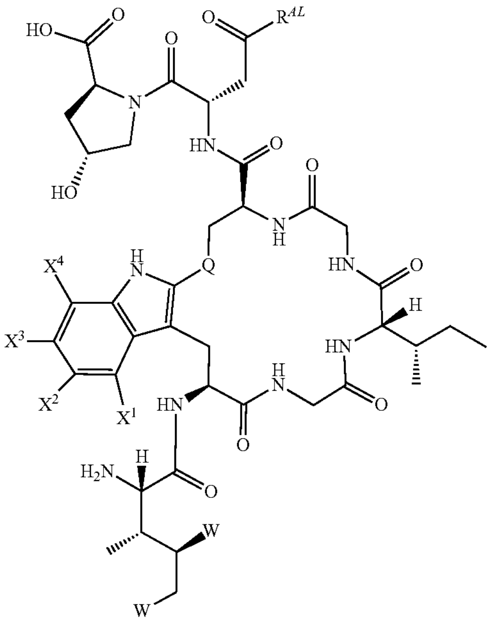

is reacted with a peptide bond forming reagent, particularly with a coupling reagent selected from a carbodiimide, an imidazolinium reagent, a phosphonium salt, an organo-phosphorous reagent, an uronium salt, a pyridinium reagent, and a phosphonic acid, more particularly with HATU, COMU, HBTU, TBTU, TOMBU, COMBU, or HCTU, in a reaction step (a), and where applicable, the compound is reacted with a deprotection agent removing $R^{PGP}$ and/or $R^{PGOH}$ and/or $R^{AL}$ and/or $R^{AMIN}$, or wherein b) a compound of formula (IIb)

(IIb)

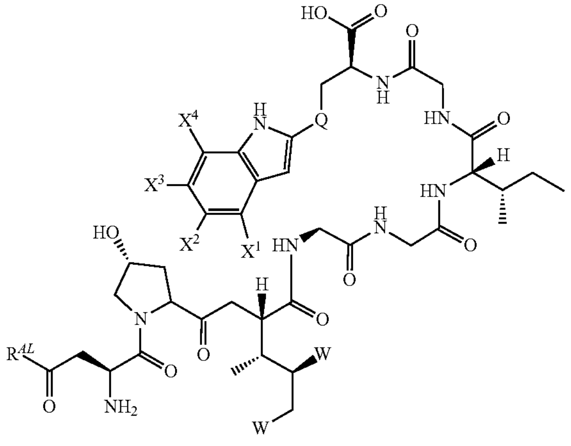

is reacted with a peptide bond forming reagent, particularly with a coupling reagent selected from a carbodiimide, an imidazolinium reagent, a phosphonium salt, an organo-phosphorous reagent, an uronium salt, a pyridinium reagent, and a phosphonic acid, more particularly with HATU, COMU, HBTU, TBTU, TOMBU, COMBU, or HCTU, in a reaction step (b), and where applicable, the compound is reacted with a deprotection agent removing $R^{PGP}$ and/or $R^{PGOH}$ and/or $R^{AL}$ and/or $R^{AMIN}$ or wherein c) a compound of formula (IIc)

(IIc)

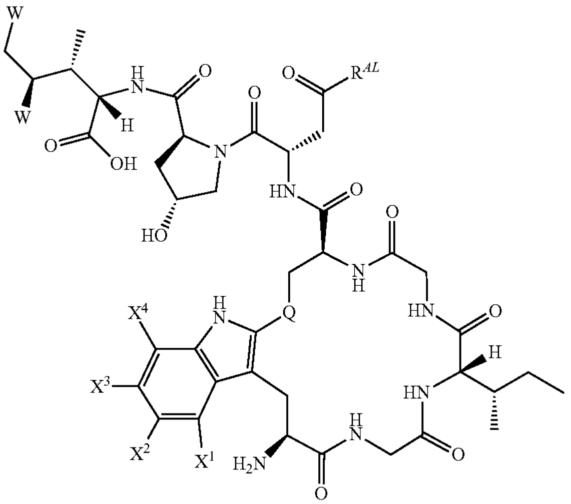

is reacted with a peptide bond forming reagent, particularly with a coupling reagent selected from a carbodiimide, an imidazolinium reagent, a phosphonium salt, an organo-phosphorous reagent, an uronium salt, a pyridinium reagent, and a phosphonic acid, more particularly with HATU, COMU, HBTU, TBTU, TOMBU, COMBU, or HCTU, in a reaction step (c), and where applicable, the compound is reacted with a deprotection agent removing $R^{PGP}$ and/or $R^{PGOH}$ and/or $R^{AL}$ and/or $R^{AMIN}$ or wherein d) a compound of formula (IId)

(IId)

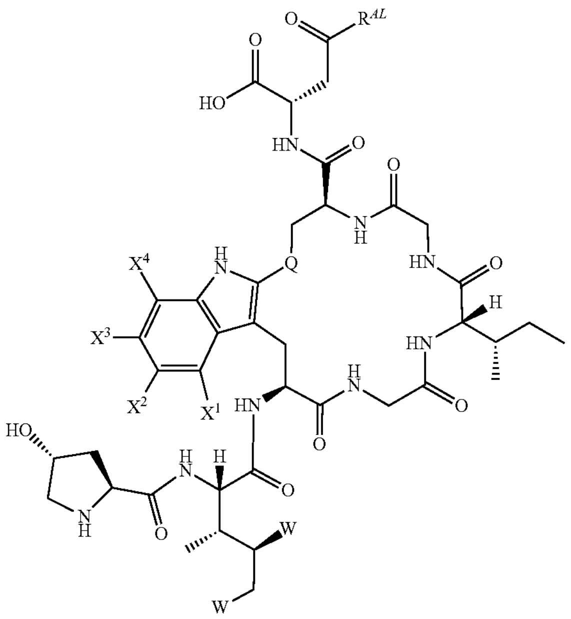

is reacted with a peptide bond forming reagent, particularly with a coupling reagent selected from a carbodiimide, an imidazolinium reagent, a phosphonium salt, an organo-phosphorous reagent, an uronium salt, a pyridinium reagent, and a phosphonic acid, more particularly with HATU, COMU, HBTU, TBTU, TOMBU, COMBU, or HCTU, in a reaction step (d), and where applicable, the compound is reacted with a deprotection agent removing $R^{PGP}$ and/or $R^{PGOH}$ and/or $R^{AL}$ and/or $R^{AMIN}$ wherein $X^1$, $X^2$, $X^3$, and $X^4$, and $Y^1$, $Y^2$, $Y^3$, and $Y^4$ are H, or one, two, three or all of $Y^1$, $Y^2$, $Y^3$, and $Y^4$ are OH or $NH_2$ and all other Y are H and the corresponding X is $NHR^{AMIN}$ or $OR^{PGP}$ and all other X are H, wherein $R^{PGP}$ is a protecting group for phenolic OH groups, particularly a phenolic OH-protecting group not acid- or alkali-labile, more particularly cleavable under reductive conditions, most particularly Cbz, or $R^{AMIN}$ is a protecting group for phenolic amino groups, particularly a phenolic amino protecting group not acid- or alkali-labile, more particularly cleavable under reductive conditions, most particularly Cbz, or one, two, three or all of $Y^1$, $Y^2$, $Y^3$, and $Y^4$ and the corresponding X are selected from F, Cl, Br, I, CN, $NO_2$, acyl, $N_3$, or alkin, and all other X and Y are H, particularly X and Y are H, or one of $Y^1$, $Y^2$, $Y^3$, and $Y^4$ is OH and the corresponding X is $OR^{PGP}$ and all other X and Y are H;

Z and W are H, or

Z is OH and W is $OR^{PGOH}$, wherein $R^{PGOH}$ is a protecting group for hydroxyl- groups, particularly a hydroxyl-protecting group cleavable with fluoride ions, $R^{AL}$ is a protected carboxyl-group or a 1-5AA peptide, particularly $R^{AL}$ is 0-allyl or O-methylester or a 1-5AA peptide, more particularly $R^{AL}$ is O-allyl or O-methylester, most particularly $R^{AL}$ is O-allyl;

V is OH or a 1-5AA peptide, particularly V is OH;

Q is S or SO.

In certain embodiments, the method is performed via step a) or step b).

In certain embodiments, the 1-5 AA peptide is composed of proteinogenic amino acids.

In certain embodiments, a compound of formula (III)

(III)

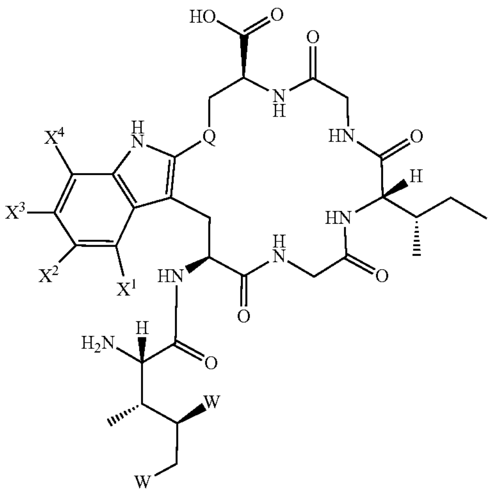

is reacted with a compound of formula (IV)

(IV)

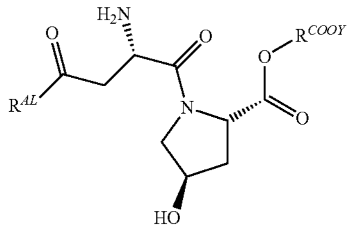

wherein $X^1$, $X^2$, $X^3$, $X^4$, W, Q, and $R^{AL}$ have the same meaning as defined above;

$R^{COOY}$ is a carboxyl-protecting group, particularly fluorenylmethyl or benzyl, more particularly fluorenylmethyl;

wherein (III) and (IV) are reacted with a peptide bond forming reagent, particularly with HATU, COMU, HBTU, TBTU, TOMBU, COMBU, or HCTU, in a reaction step (e)

to yield the compound characterized by (IIa).

In certain embodiments, a compound of formula (V)

(V)

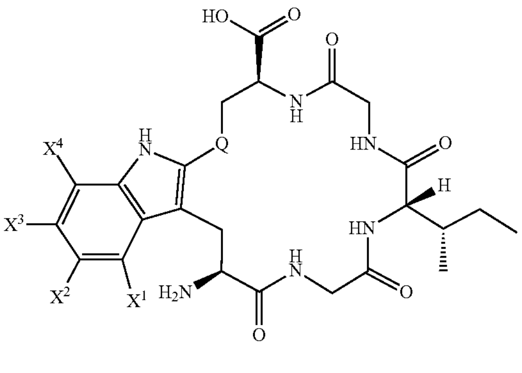

is reacted with a compound of formula (VI)

(VI)

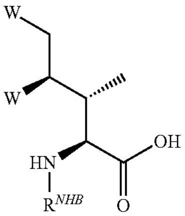

wherein $X^1$, $X^2$, $X^3$, $X^4$, Q, and W have the same meaning as defined above;

$R^{NHB}$ is an amino protecting group, particularly an amino protecting group cleavable under alkaline conditions, more particularly Fmoc, wherein the amino-group of (V) is preactivated, particularly with MSA, and preactivated (V) and (VI) are reacted with a peptide bond forming reagent, particularly with HATU, COMU, HBTU, TBTU, TOMBU, COMBU, or HCTU, more particularly with COMU, in a reaction step (f) to yield the compound (III).

In certain embodiments, a compound of formula (V)

(V)

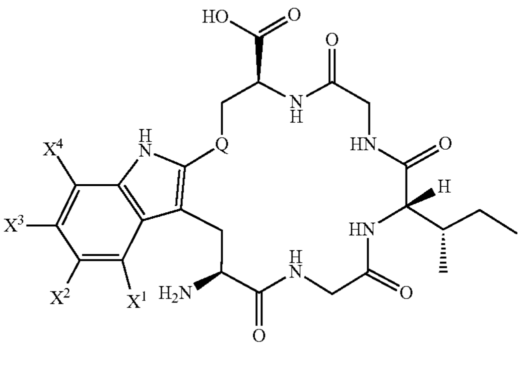

is reacted with a compound of formula (VII)

(VII)

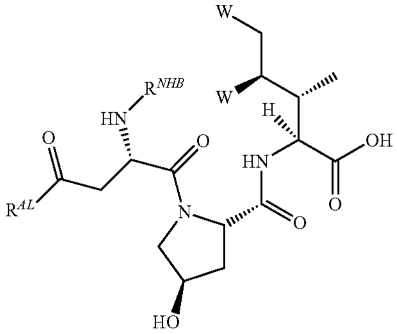

wherein $X^1$, $X^2$, $X^3$, $X^4$, W, Q, $R^{NHB}$, and $R^{AL}$ have the same meaning as defined above;

wherein the amino-group of (V) is preactivated, particularly with MSA, and preactivated (V) and (VII) are reacted with a peptide bond forming reagent, particularly with HATU, or the amino-group of (V) is preactivated, particularly with MSA, and the carboxyl-group of compound (VII) is preactivated, particularly with an O-PFP-ester, O-PCP-ester, or OSu-ester, and preactivated (V) and preactivated (VII) are reacted, in a reaction step (g) to yield the compound (IIb).

For coupling compounds (V) and (VII), the acid-COOH group of compound (V) does not need to be protected. No significant side reactions were observed without protecting group.

In certain embodiments, a compound of formula (V)

(V)

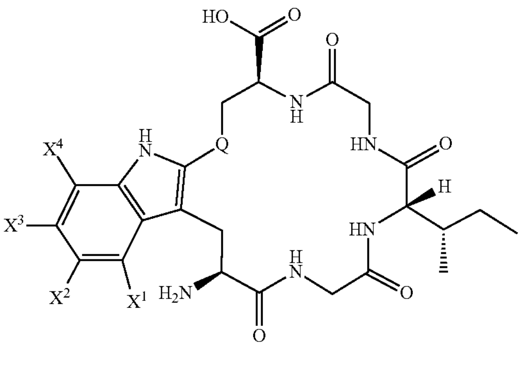

is reacted with a compound of formula (VII)

(VII)

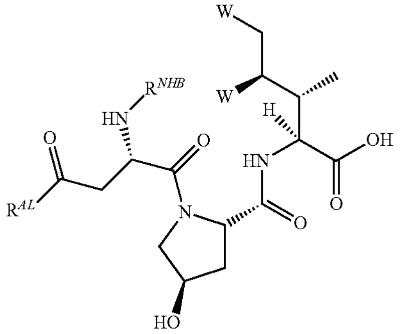

wherein $X^1$, $X^2$, $X^3$, $X^4$, W, Q, $R^{NHB}$, and $R^{AL}$ have the same meaning as defined above;

wherein (V) and (VII) are reacted with a peptide bond forming reagent, particularly with HATU, COMU, HBTU, TBTU, TOMBU, COMBU, or HCTU, to yield the compound (IIc).

In certain embodiments, a compound of formula (XVI)

(XVI)

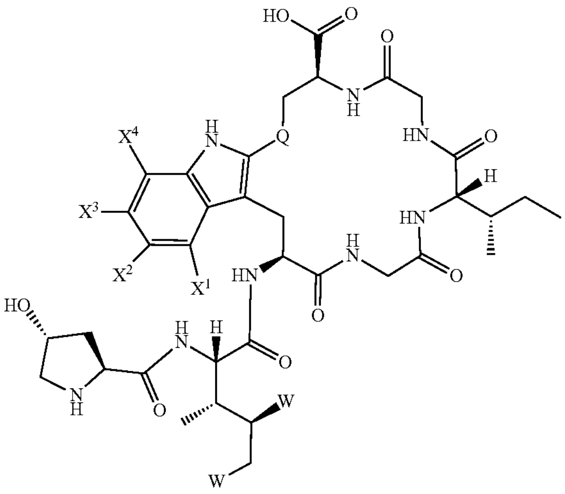

is reacted with a compound of formula (XVII)

(XVII)

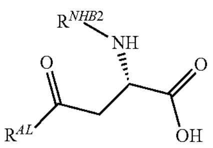

wherein $X^1$, $X^2$, $X^3$, $X^4$, W, Q, and $R^{AL}$ have the same meaning as defined above;

$R^{NHB2}$ is an amino-protecting group, particularly an amino-protecting group cleavable under acidic conditions, more particularly Boc;

wherein the amino-group of (XVI) is preactivated, particularly with MSA, and preactivated (XVI) and (XVII) are reacted with a peptide bond forming reagent, particularly with HATU, or the amino-group of (XVI) is preactivated, particularly with MSA, and the carboxyl-group of compound (XVII) is preactivated, particularly with an O-PFP-ester, O-PCP-ester, or OSu-ester, and preactivated (XVI) and preactivated (XVII) are reacted, to yield the compound (IId).

In certain embodiments, a compound of formula (V)

(V)

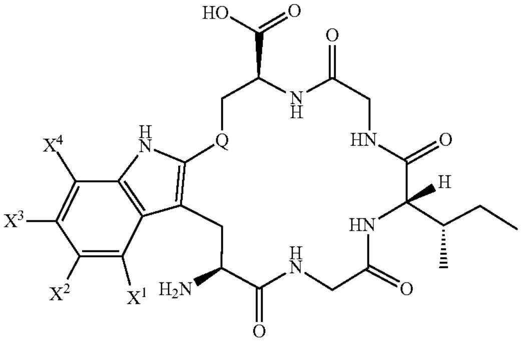

is reacted with a compound of formula (XVIII)

(XVII)

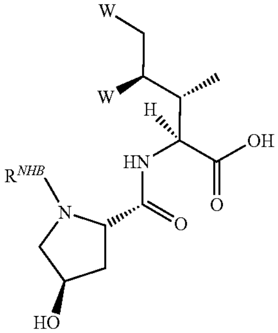

wherein $X^1$, $X^2$, $X^3$, $X^4$, W, Q, $R^{NHB}$, and $R^{AL}$ have the same meaning as defined above;

wherein the amino-group of (V) is preactivated, particularly with MSA, and preactivated (V) and (XVIII) are reacted with a peptide bond forming reagent, particularly with HATU, or the amino-group of (V) is preactivated, particularly with MSA, and the carboxyl-group of compound (XVIII) is preactivated, particularly with an O-PFP-ester, O-PCP-ester, or OSu-ester, and preactivated (V) and preactivated (XVIII) are reacted, to yield the compound (XVI).

In certain embodiments, for a compound of formula (Idesox)

(I)

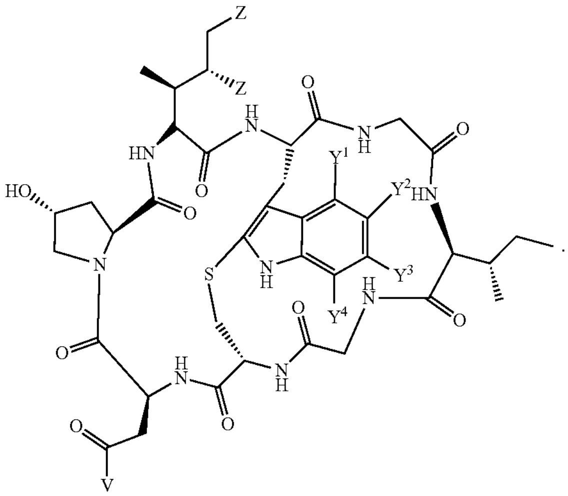

wherein $Y^1$, $Y^2$, $Y^3$, $Y^4$, Z, Q, and V have the same meaning as defined above; the sulfur atom is oxidized.

In certain embodiments, the oxidation of the sulfur atom is performed using manganese ions.

In certain embodiments, the compound is reacted with a compound of formula (XV)

(XV)

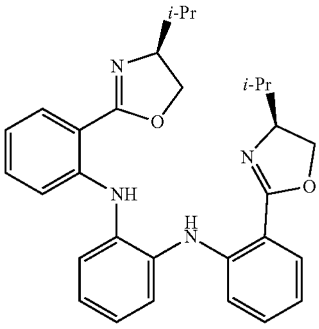

and with Mn(OTD$_2$ and $H_2O_2$,

In certain embodiments, the oxidation of the sulfur atom is performed using PPO, dibenzyolperoxide, tert-butyl peroxybenzoate, or lauroyl peroxide. Preparation of PPO is described in (S. Gan, J. Yin, Y. Yao, Y. Liu, D. Chang, D. Zhu, L. Shi, *Org. Biomol. Chem.* 2017, 15, 2647-2654.).

In certain embodiments, the oxidation of the sulfur atom is performed with mCPBA (meta-chloroperoxybenzoic acid) in isopropanol/ethanol (8:3).

In certain embodiments, the oxidation of the sulfur atom is performed with an oxaziridinium salt as described in (Rio et al, Org. Lett. 2007, 9, 12, 2265-2268).

In certain embodiments, the oxidation of the sulfur atom is performed with non-enantio-selective agents or simply with oxygen or hydrogen peroxide.

In certain embodiments, the oxidation of the sulfur atom is performed using iodine and oxygen.

The oxidation of the sulfur atom is performed in a reaction step (h) to yield the compound (Iox)

(Iox)

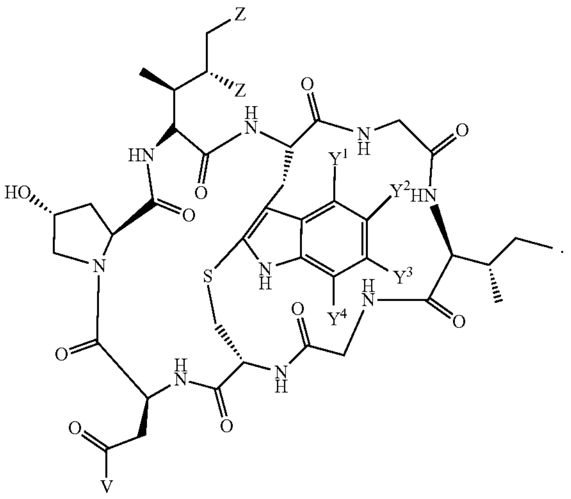

In certain embodiments, for a compound of formula (Vdesox)

(Vdesox)

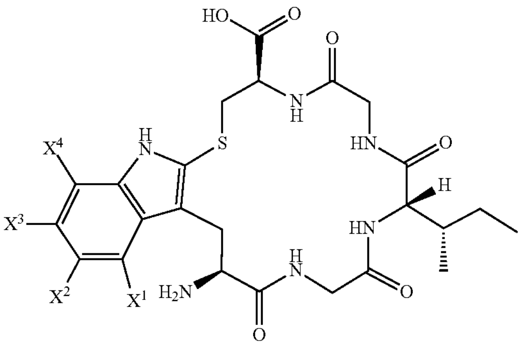

wherein $X^1$, $X^2$, $X^3$, and $X^4$ have the same meaning as defined above;

the sulfur atom is oxidized.

In certain embodiments, the oxidation of the sulfur atom is performed using manganese ions.

In certain embodiments, the compound is reacted with a compound of formula (XV)

(XV)

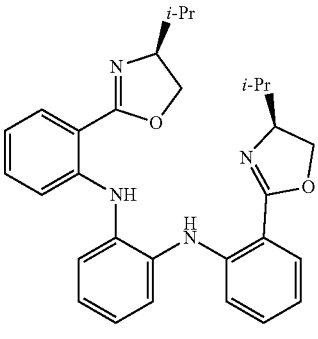

and with $Mn(OTf)_2$ and $H_2O_2$,

In certain embodiments, the oxidation of the sulfur atom is performed using PPO, dibenzyolperoxide, tert-butyl peroxybenzoate, or lauroyl peroxide. Preparation of PPO is described in (S. Gan, J. Yin, Y. Yao, Y. Liu, D. Chang, D. Zhu, L. Shi, Org. Biomol. Chem. 2017, 15, 2647-2654.).

In certain embodiments, the oxidation of the sulfur atom is performed with mCPBA (meta-chloroperoxybenzoic acid) in isopropanol/ethanol (8:3).

In certain embodiments, the oxidation of the sulfur atom is performed with an oxaziridinium salt as described in (Rio et al, *Org. Lett.* 2007, 9, 12, 2265-2268).

In certain embodiments, the oxidation of the sulfur atom is performed with non-enantio-selective agents or simply with oxygen or hydrogen peroxide.

In certain embodiments, the oxidation of the sulfur atom is performed using iodine and oxygen.

The oxidation of the sulfur atom is performed in a reaction step (i) to yield the compound (Vox)

(Vox)

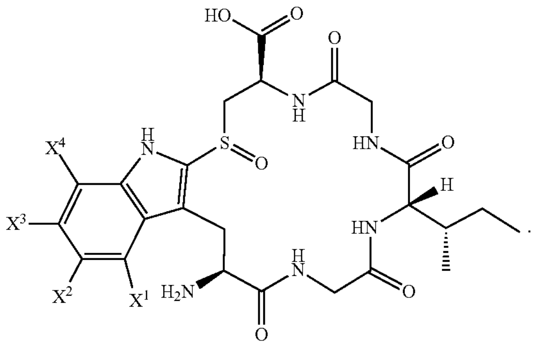

In certain embodiments, a compound of formula (VIII)

(VIII)

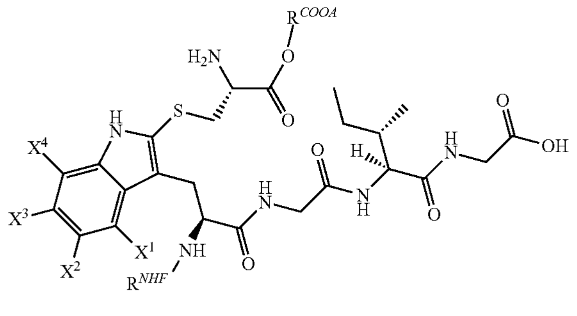

wherein $R^{NHF}$ is an amino protecting group, particularly an amino protecting group cleavable with fluoride ions or strong acids, more particularly Teoc, or an amino protecting group cleavable with alkaline conditions, more particularly Fmoc, $R^{COOA}$ is a carboxyl-protecting group, particularly a carboxyl-protecting group cleavable under strongly acidic conditions, more particularly tert-butyl, $X^1$, $X^2$, $X^3$, and $X^4$ have the same meaning as outlined above, is reacted with a peptide bond forming reagent, particularly with a coupling reagent selected from a carbodiimide, an imidazolinium reagent, a phosphonium salt, an organo-phosphorous reagent, an uronium salt, a pyridinium reagent, and a phosphonic acid, more particularly with T3P, HATU, COMU, HBTU, TBTU, TOMBU, COMBU, or HCTU, in a reaction step (j), and the compound is reacted with a deprotection agent removing $R^{NHF}$ and $R^{COOA}$ in a reaction step (k), particularly with TFA, to yield the compound characterized by (Vdesox) or (V).

In certain embodiments, a compound of formula (IX)

(IX)

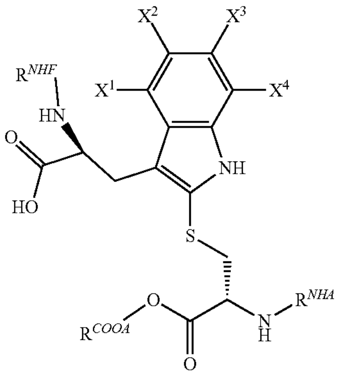

is reacted with a compound of formula (X)

(X)

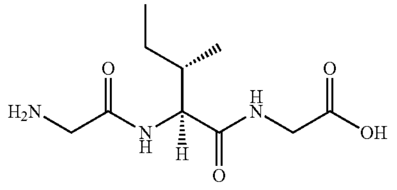

wherein $R^{NHA}$ is an amino protecting group, particularly an amino protecting group cleavable under acidic conditions, more particularly Boc, $R^{COOA}$ $R^{NHF}$ and $X^1$, $X^2$, $X^3$, and $X^4$ have the same meaning as outlined above, wherein compound (VII) is preactivated with a peptide bond forming reagent, particularly with HATU, COMU, HBTU, TBTU, TOMBU, COMBU, or HCTU, followed by a reaction with the silylated compound (VIII), or is preactivated as in OSu-ester, followed by a reaction with the compound (VII) in a reaction step (I), and the compound is reacted with a deprotection agent removing $R^{NHA}$ in a reaction step (m), particularly with acidic conditions, more particularly at a pH of −3 to 0, even more particularly with HCl or p-toluenesulfonic acid, most particularly with 2 M HCl in Dioxan, to yield the compound characterized by (VIII).

In certain embodiments, a compound of formula (XI)

(XI)

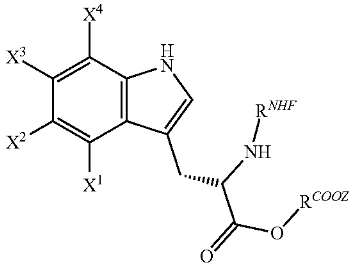

is reacted with a compound of formula (XII)

(XII)

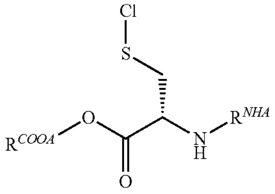

wherein $R^{COOZ}$ is a carboxyl-protecting group, particularly a carboxyl-protecting group cleavable with Zn, more particularly Tce, or $R^{COOZ}$ is H, $R^{COOA}$, $R^{NHF}$, $R^{NHA}$ and $X^1$, $X^2$, $X^3$, and $X^4$ have the same meaning as outlined above, are reacted in a reaction step (n), and if $R^{COOZ}$ is a carboxyl-protecting group, the compound is reacted with a deprotection agent removing $R^{COOZ}$ in a reaction step (o), particularly with Zn, to yield the compound characterized by (IX).

A protection group strategy was applied that relies on acid stability. Decreasing pH values were used for deprotection. First, the Tce group of tryptophan ($R^{COOZ}$ of compound VIII) was removed under reductive conditions using Zn with mildly acidic pH. Afterwards, the Boc group of cysteine ($R^{NHA}$ of compound IX) was removed with p-toluenesulfonic acid. Last, Teoc ($R^{NHF}$) and tert-butyl ($R^{COOA}$) of compound (V) were removed concomitantly with 95% TFA.

In certain embodiments, a compound of formula (VI)

(VI)

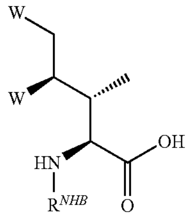

is reacted with a compound of formula (XIII)

(XIII)

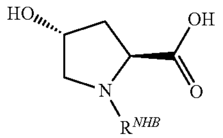

and a compound of formula (XIV)

(XIV)

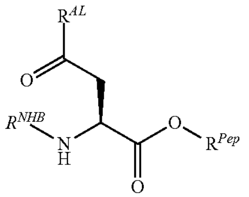

wherein $R^{AL}$ has the same meaning as described above, $R^{Pep}$ is an active ester, particularly O-pentafluorophenol or OSu-ester, $R^{NHB}$ is an amino protecting group, particularly an amino protecting group cleavable under alkaline conditions, more particularly Fmoc, are reacted with solid phase peptide synthesis in a reaction step (p), wherein the carboxyl-group of compound (XIV) may be protected, to yield the compound characterized by (VII).

Another aspect of the invention relates to a compound of the general formula (I)

(I)

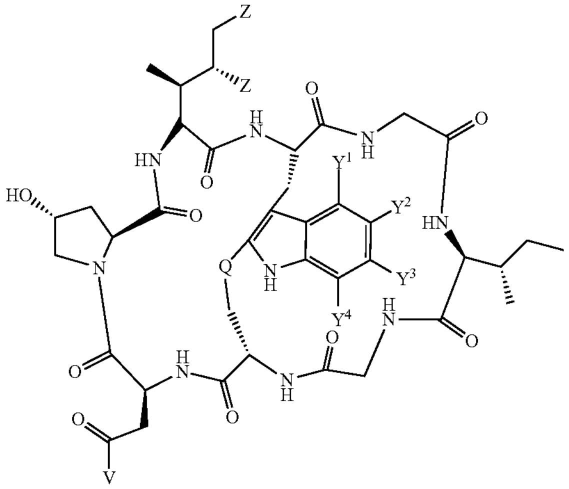

wherein one, two, or three of $Y^1$, $Y^2$, and $Y^4$ are OH and all other Y are H, or one, two, three or all of $Y^1$, $Y^2$, $Y^3$, and $Y^4$ are selected from F, Cl, Br, and I and all other Y are H, particularly one of $Y^1$, $Y^2$, and $Y^4$ is OH and all other Y are H;

Z is H, or

Z is OH,

V is OH or a 1-5AA peptide, particularly V is OH,

Q is S or SO.

Another aspect of the invention relates to a compound of the general formula (IIa)

(IIa)

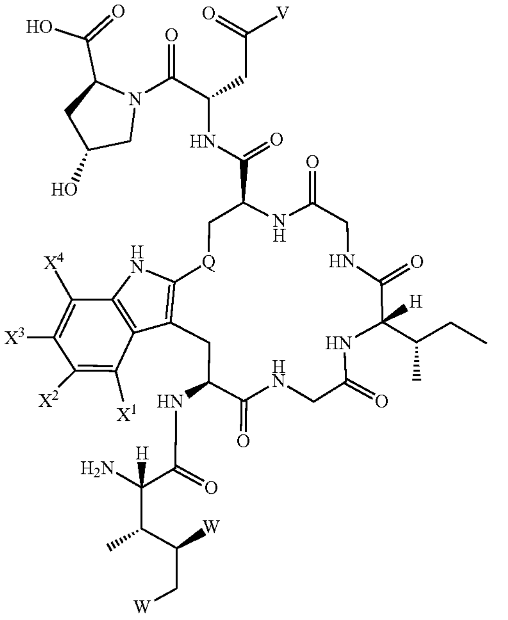

wherein $X^1$, $X^2$, $X^3$, and $X^4$, are H, or one, two, three or all of $X^1$, $X^2$, $X^3$, and $X^4$ are OH and all other X are H, or one, two, three or all of $X^1$, $X^2$, $X^3$, and $X^4$ are selected from F, Cl, Br, and I and all other X are H, particularly $X^1$, $X^2$, $X^3$, and $X^4$ are H, or one of $X^1$, $X^2$, $X^3$, and $X^4$ is OH and all other X are H;

W is H, or

W is OH,

V is OH or a 1-5AA peptide, particularly V is OH,

Q is S or SO.

Another aspect of the invention relates to a compound of the general formula (IIb)

(IIb)

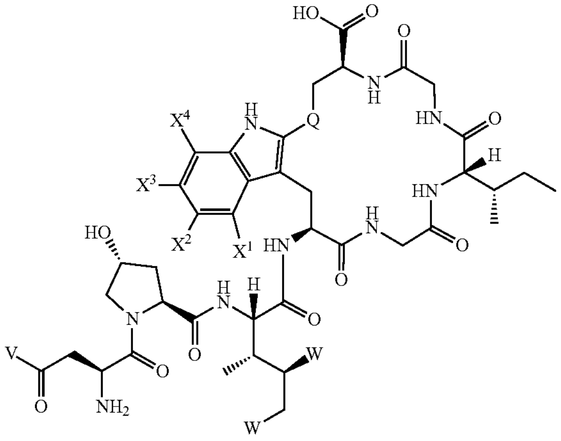

wherein $X^1$, $X^2$, $X^3$, and $X^4$, are H, or one, two, three or all of $X^1$, $X^2$, $X^3$, and $X^4$ are OH and all other X are H, or one, two, three or all of $X^1$, $X^2$, $X^3$, and $X^4$ are selected from F, Cl, Br, and I and all other X are H, particularly $X^1$, $X^2$, $X^3$, and $X^4$ are H, or one of $X^1$, $X^2$, $X^3$, and $X^4$ is OH and all other X are H;

W is H, or

W is OH,

V is OH or a 1-5AA peptide, particularly V is OH,

Q is S or SO.

Another aspect of the invention relates to a compound of the general formula (III)

(III)

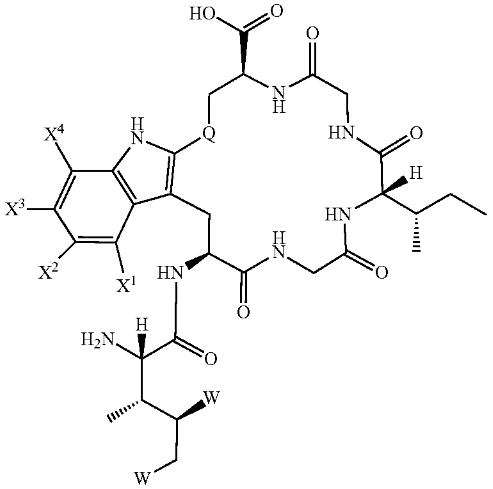

wherein one, two, or all of $X^1$, $X^2$, and $X^4$ are OH and all other X are H, or one, two, or all of $X^1$, $X^2$, and $X^4$ are selected from F, Cl, Br, and I and all other X are H, particularly one of $X^1$, $X^2$, and $X^4$ is OH and all other X are H;

W is H, or

W is OH,

Q is S or SO.

Another aspect of the invention relates to a compound of the general formula (V)

(V)

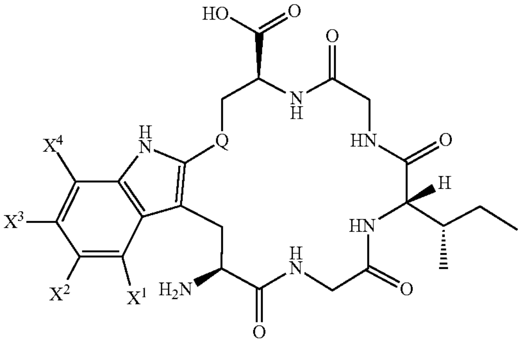

wherein one, two, or all of $X^1$, $X^2$, and $X^4$ are OH and all other X are H, or one, two, or all of $X^1$, $X^2$, and $X^4$ are selected from F, Cl, Br, and I and all other X are H, particularly one of $X^1$, $X^2$, and $X^4$ is OH and all other X are H, Q is S or SO.

The invention is further illustrated by the following examples and figures, from which further embodiments and advantages can be drawn. These examples are meant to illustrate the invention but not to limit its scope.

DESCRIPTION OF THE FIGURES

FIG. 1 Synthesis of the dipeptide building block H-Asp (OAII)-Hyp-OFm∘HCl (3).

Figure 2:
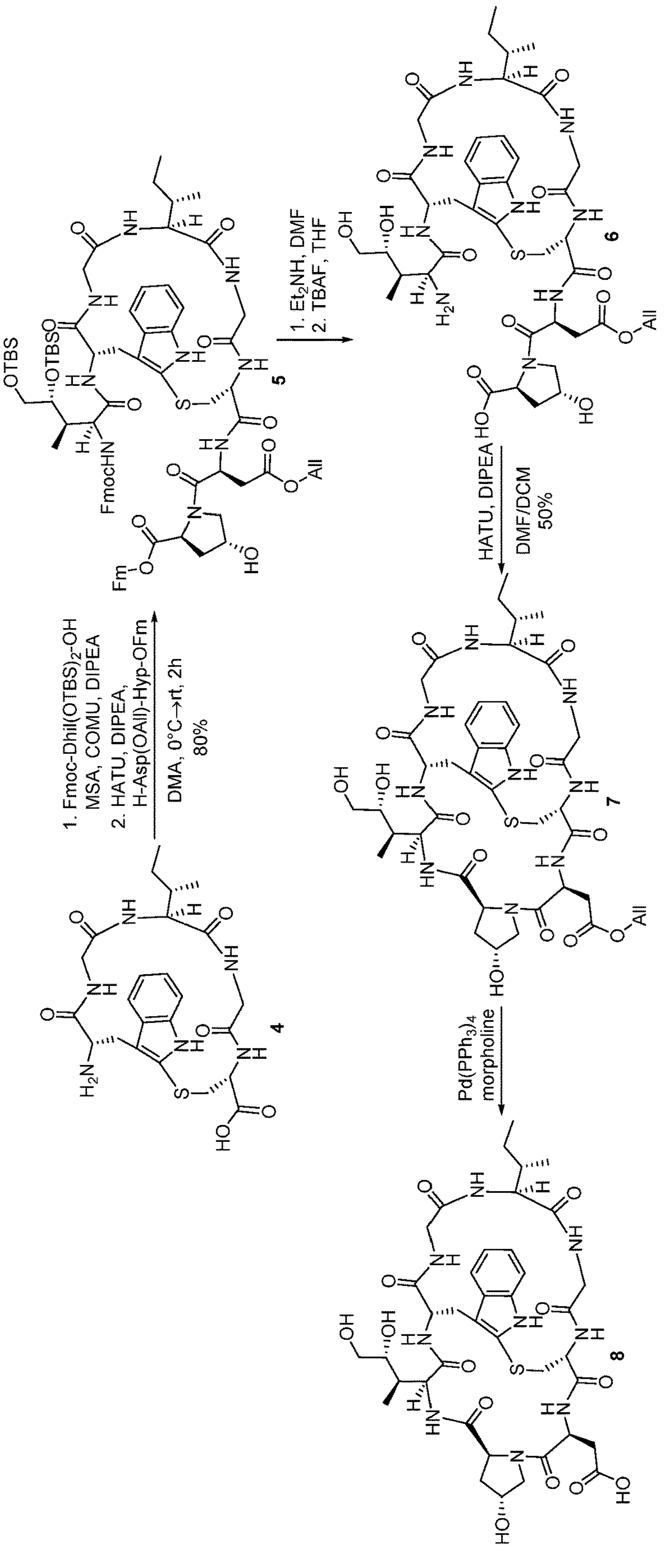
FIG. 2 Synthesis of Deoxyamanin.

FIG. 2 Synthesis of Deoxyamanin.

EXAMPLES

Synthesis of $(N\text{-Boc})_2$-cystine-$(OtBu)_2$ (35)

35

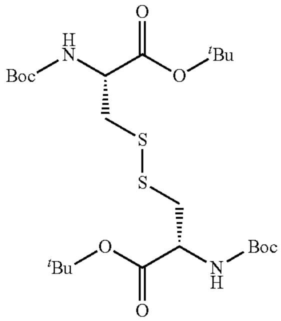

A solution of L-cystine-$(OtBu)_2$ (34, 10 g, 24 mmol, 1.0 eq.) in a 1:1 mixture of $H_2O$/dioxane (240 mL) was treated with $NaHCO_3$ (8.06 g, 96.0 mmol, 4.00 eq.) and $Boc_2O$ (10.1 mL, 47.0 mmol, 2.00 eq.) and the reaction mixture was stirred for 16 h at r.t. The reaction mixture was concentrated under reduced pressure and the aqueous layer was extracted with EtOAc (3×120 mL). The organic layer was washed with brine (100 mL), dried over $Na_2SO_4$ and the solvent was removed under reduced pressure to afford 35 (13.2 g, 24.0 mmol, quant.) as a pale yellow solid.

HRMS (ESI): m/z calc for $C_{24}H_{44}N_2O_8S_2(M+H)^+$ 553.2612, found 553.2615.

tert-butyl S-(6-(benzyloxy)-3-((S)-3-oxo-3-(2,2,2-trichloroethoxy)-2-(((2-(trimethylsilyl)ethoxy) carbonyl)amino)propyl)-1H-indol-2-yl)-N-(tert-butoxy-carbonyl)-L-cysteinate (40)

40

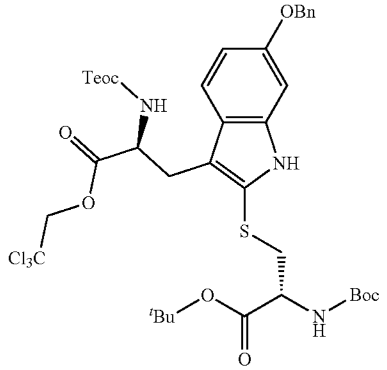

To a solution of $(N\text{-Boc})_2$-L-Cystin-$(OtBu)_2$ (35, 900 mg, 1.63 mmol, 1.00 eq.) in $CHCl_3$ (16.3 mL) was added $SO_2Cl_2$ (263 μL, 3.26 mmol, 2.00 eq.). After the reaction mixture was stirred for 1 h at r.t. the solvent was removed under reduced pressure. The residue was redissolved in $CHCl_3$ (16.3 mL) and cooled to 0° C. and added to an ice cold solution of 39 (800 mg, 1.67 mmol, 1.00 eq.) and $NaHCO_3$ (420 mg, 5.00 mmol, 3.00 eq.) in $CHCl_3$ (16.7 mL) dropwise over a period of 10 min. Afterwards the reaction mixture was stirred for 15 min at 0° C. and 1 h at r.t. The organic layer was washed with $H_2O$ (10 mL) and sat. $NaHCO_3$-solution (10 mL). After drying of the organic layer with $Na_2SO_4$ and removal of the solvent under reduced pressure the crude product of 40 was used in the next step without further purification.

HRMS (ESI): m/z calc. for $C_{38}H_{52}Cl_3N_3O_9SSi$ $(M+H)^+$ 860.2332, found 860.2323.

tert-butyl N-(tert-butoxycarbonyl)-S-(3-((S)-3-oxo-3-(2,2,2-trichloroethoxy)-2-(((2-(trimethylsilyl) ethoxy)carbonyl)amino)propyl)-1H-indol-2-yl)-L-cysteinate (41)

41

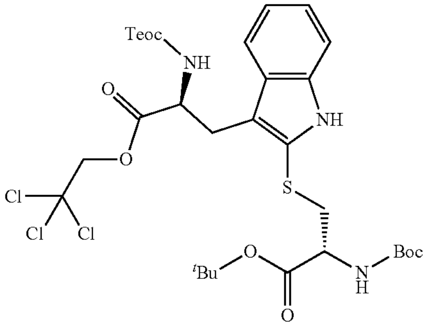

To a solution of $(N\text{-Boc})_2$-L-Cystin-$(OtBu)_2$ (39, 5.06 g, 9.15 mmol, 1.00 eq.) in $CHCl_3$ (92 mL) was added $SO_2Cl_2$ (1.48 mL, 18.3 mmol, 2.00 eq.). After the reaction mixture was stirred for 1 h at r.t. the solvent was removed under reduced pressure. The residue was redissolved in $CHCl_3$ (92 mL), cooled to 0° C. and added dropwise to an ice cold solution of 38 (4.4 g, 9.17 mmol 1.00 eq.) and $NaHCO_3$ (2.31 g, 27.5 mmol, 3.00 eq.) in $CHCl_3$ (92 mL) over a period of 10 min. Afterwards the reaction mixture was stirred for 15 min at 0° C. and 1 h at r.t. The organic layer was washed with $H_2O$ (2×100 mL) and sat. $NaHCO_3$-solution (2×80 mL). After drying of the organic layer with $Na_2SO_4$ and removal of the solvent under reduced pressure the crude product of 41 was used in the next step without further purification.

HRMS (ESI): m/z calc. for $C_{31}H_{46}Cl_3N_3O_8SSi$ $(M+H)^+$ 754.1913, found 754.1917.

(S)-3-(6-(benzyloxy)-2-(((R)-3-(tert-butoxy)-2-((tert-butoxycarbonyl)amino)-3-oxopropyl)thio)-1H-indol-3-yl)-2-(((2-(trimethylsilyl)ethoxy)carbonyl)amino) propanoic acid (49)

49

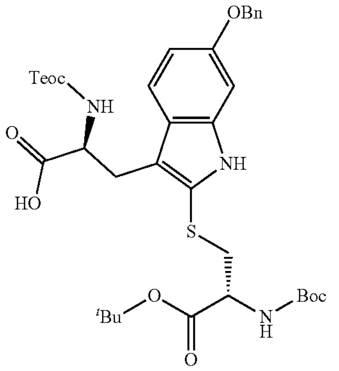

A solution of tryptathionine derivative 39 (1.63 mmol, 1.00 eq.) in DMF (8.4 mL) was treated with $CH_3COOH$ (0.8 mL) and zinc (3.51 g, 53.6 mmol, 33.0 eq.) for 2 h at 45° C. The reaction mixture was filtered over Celite and the solvent was removed under reduced pressure. The crude product was dissolved in EtOAc (50 mL) and washed with 10% $KHSO_4$ solution (2×25 mL) and brine (2×25 mL). After drying over $Na_2SO_4$ and removing of the solvent under reduced pressure, the crude product was purified by C18 reverse phase chromatography (AcN/$H_2O$ 50% to 100% gradient) to give compound 49 as a yellow solid (840 mg, 83% over 2 steps).

HRMS (ESI): m/z calc. for $C_{36}H_{51}N_3O_9SSi$ $(M+H)^+$ 730.3183, found 730.3188.

(S)-3-(2-(((R)-3-(tert-butoxy)-2-((tert-butoxycarbonyl)amino)-3-oxopropyl)thio)-1H-indol-3-yl)-2-(((2-(trimethylsilyl)ethoxy)carbonyl)amino)propanoic acid (50)

50

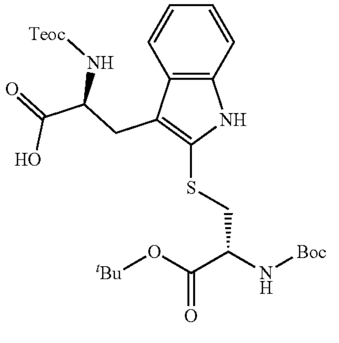

A solution of tryptathionine derivative 38 (9.15 mmol, 1.00 eq.) in DMF (40 mL) was treated with $CH_3COOH$ (4 mL) and zinc (20.0 g, 302 mmol, 33.0 eq.) for 2 h at 45° C. The reaction mixture was filtered over Celite and the solvent was removed under reduced pressure. The crude product was dissolved in EtOAc (200 mL) and washed with 10% $KHSO_4$ solution (2×50 mL) and brine (2×50 mL). After drying over $Na_2SO_4$ and removing of the solvent under reduced pressure, the crude product was purified by C18 reverse phase chromatography (AcN/$H_2O$ 50% to 100% gradient) to afford compound 50 as a yellow oil (5.0 g, 88%. over 2 steps).

HRMS (ESI): m/z calc. for $C_{31}H_{46}Cl_3N_3O_8SSi$ $(M+H)^+$ 624.2769, found 624.2775.

((benzyloxy)carbonyl)glycyl-L-isoleucine (44)

44

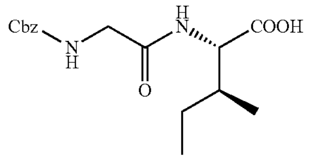

To a solution of Cbz-glycine (42, 10.0 g, 32.7 mmol, 1.00 eq.) in acetone (100 mL) was added a suspension of L-isoleucine (4.71 g, 35.9 mmol, 1.10 eq.) and $NaHCO_3$ (8.23 g, 87.9 mmol, 3.00 eq.) in water (100 mL). The reaction mixture was stirred at r.t. for 3 h and concentrated under reduced pressure. The aqueous layer was carefully acidified to pH=4 by dropwise addition of 1 M HCl and extracted with EtOAc (3×150 mL). The organic phase was then washed with brine (2×100 mL), dried over $Na_2SO_4$ and evaporated under reduced pressure to afford the product 44 as a colourless oil (10.1 g, 96%).

HRMS (ESI): m/z calc. for $C_{16}H_{22}N_2O_5$ $(M+H)^+$ 323.1601, found 323.1606.

Glycyl-L-isoleucylglycine (45)

45

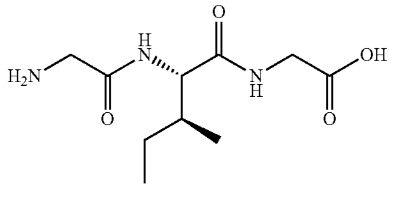

Dipeptide 44 (10.1 g, 31.3 mmol, 1.00 eq.) and benzyl glycinate (8.21 g, 40.7 mmol, 1.30 eq.) were dissolved in dry DMF (125 mL). Then, COMU (17.4 g, 40.7 mmol, 1.30 eq.) and DIPEA (12.6 mL, 72.1 mmol, 3.00 eq.) were added at 0° C. The reaction mixture was allowed to warm to r.t. overnight and diluted with EtOAc (300 mL) afterwards. After washing with a solution of 10% $KHSO_4$-solution (2×100 mL) the fully protected tripeptide precipitated in the organic phase. The organic phase was cooled to 4° C. for 4 h in order for the peptide to precipitate, then the precipitate was filtered and washed with cold EtOAc. The precipitate was redissolved in a 1:1 mixture of water and THF (260 mL). Pd/C (1 g) was added to the solution after degassing with $N_2$ for 30 min. Then, the reaction mixture was degassed with hydrogen for 1 h. After vigorous stirring at room temperature under 1.0 atm of hydrogen overnight, the catalyst was filtered through a pad of Celite. Afterwards, the mixture was concentrated under reduced pressure to obtain the product 45 as a white solid (5.71 g, 74%) HRMS (ESI): m/z calc. for $C_{10}H_{19}N_3O_4$ $(M+H)^+$ 246.1448, found 246.1440.

Synthesis of Pentapeptide 51

51

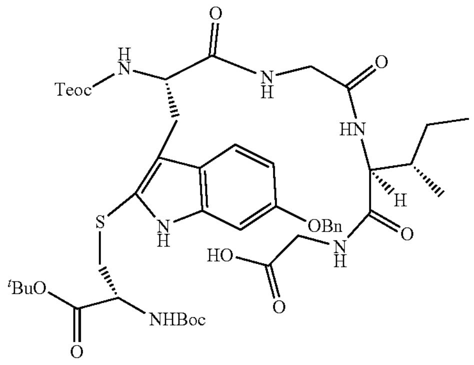

A solution of thioether building block 49 (111 mg, 0.14 mmol, 1.00 eq.) in AcN (0.7 mL) was treated with collidine (37 μL, 0.27 mmol, 2.0 eq) and N,N'-disuccinimidyl carbonate (39 mg, 0.15 mmol, 1.1 eq.) and stirred for 1 h at r.t. A solution of tripeptide 45 (44 mg, 0.18 mmol, 1.3 eq) in a 1:4 mixture of AcN/$H_2O$ (1 mL) was added and the reaction mixture was stirred for 2 h at r.t. Afterwards, the mixture was diluted with EtOAc (20 mL), 10% $KHSO_4$-solution (20 mL) was added and the aqueous layer was extracted with EtOAc (2×20 mL). The organic layer was washed with brine (2×20 mL), dried over $Na_2SO_4$ and evaporated under reduced pressure which afforded pentapeptide 51 as a yellow solid (115 mg, 90%).

HRMS (ESI): m/z calc. for $C_{46}H_{68}N_6O_{12}SSi$ $(M+H)^+$ 957.4458, found 957.4457.

Synthesis of Pentapeptide 52

52

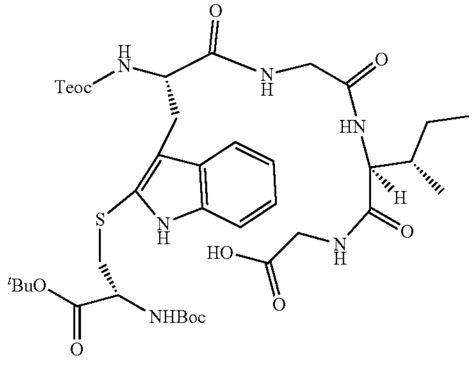

A solution of tryptathionine building block 50 (2.0 g, 2.5 mmol, 1.0 eq.) in AcN (10 mL) was treated with collidine (659 μL, 4.95 mmol, 2.00 eq) and N,N'-disuccinimidyl carbonate (697 mg, 2.72 mmol, 1.10 eq.) and stirred for 1 h at r.t. A solution of tripeptide 45 (790 mg, 3.22 mmol, 1.30 eq.) in a 1:4 mixture of AcN/$H_2O$ (18 mL) was added and the reaction mixture was stirred for 2 h at r.t. Afterwards, the mixture was diluted with EtOAc (100 mL), 10% $KHSO_4$-solution (20 mL) was added and the aqueous layer was extracted with EtOAc (2×50 mL). The organic layer was washed with brine (2×50 mL), dried over $Na_2SO_4$ and evaporated under reduced pressure which afforded pentapeptide 52 as a yellow solid (2.15 g, 93%).

HRMS (ESI): m/z calc. for $(M+H)^+$ $C_{36}H_{51}Cl_3N_6O_{11}S$ 851.4039, found 851.4058.

Fully Protected Cyclic Pentapeptide 53

53

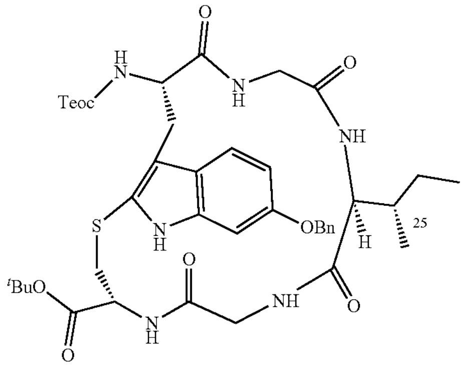

Pentapeptide 51 (151 mg, 0.180 mmol, 1.00 eq.) was dissolved in 1 mL of a solution of p-toluenesulfonic acid in THF (1.8 M) and was stirred for 4 h at r.t. Then, the reaction mixture was neutralized by the addition of DIPEA (320 μL, 1.84 mmol, 10 eq) and diluted with DCM (180 mL). Afterwards, DIPEA (60.2 μL, 354 μmol, 2.00 eq.) and T3P (50% in EtOAc, 210 μL, 354 μmol, 0.34 eq.) were added. After the solution was stirred for 16 h at r.t. ⅔ of the solvent was concentrated under reduced pressure. The organic phase was washed with 10% $KHSO_4$-solution (20 mL), sat. $NaHCO_3$-solution (20 mL), water (20 mL) and brine (20 mL). The organic layer was dried over $Na_2SO_4$ and the solvent was removed under reduced pressure. The crude product was purified by C18 reverse phase chromatography (AcN/$H_2O$ 50% to 100% gradient) to afford cyclic pentapeptide 53 as a yellow solid (82 mg, 70%)

HRMS (ESI): m/z calc. for $C_{41}H_{58}N_6O_9SSi$ $(M+H)^+$ 839.3828, found 839.3839.

Fully Protected Cyclic Pentapeptide (54)

54

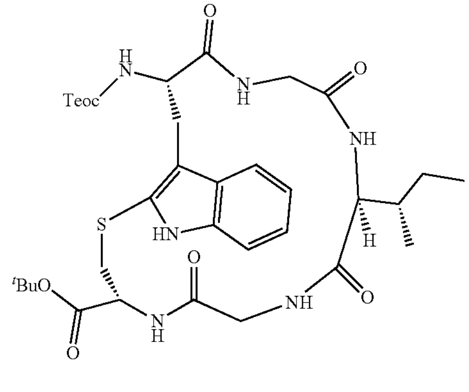

Pentapeptide 52 (700 mg, 0.822 mmol, 1.00 eq.) was dissolved in 10 mL of 2 M HCl in dioxane and stirred for 40 min at r.t. Then, the reaction mixture diluted with 40 mL of dioxane and the solvent was evaporated under reduced pressure. The precipitate was dissolved in 8 mL DMF and diluted with 82 mL DCM. Afterwards, DIPEA (279 μL, 1.64 mmol, 2.00 eq.) and T3P (50% in EtOAc, 977 μL, 1.64 mmol, 2.00 eq.) were added. After the solution was stirred for 5 h at r.t., ⅓ of the solvent was concentrated under reduced pressure. The organic phase was washed with 10% $KHSO_4$-solution (20 mL), sat. $NaHCO_3$-solution (20 mL), water (20 mL) and brine (20 mL). The organic layer was dried over $Na_2SO_4$ and the solvent was removed under reduced pressure. The crude product was purified by C18 reverse phase chromatography (AcN/$H_2O$ 50% to 100% gradient) to afford cyclic pentapeptide 54 as a yellow solid (420 mg, 72%).

HRMS (ESI): m/z calc. for $C_{34}H_{52}N_6O_8SSi$ $(M+H)^+$ 733.3409, found 733.3409.

Fully Deprotected Monocyclic Pentapeptide 55

55

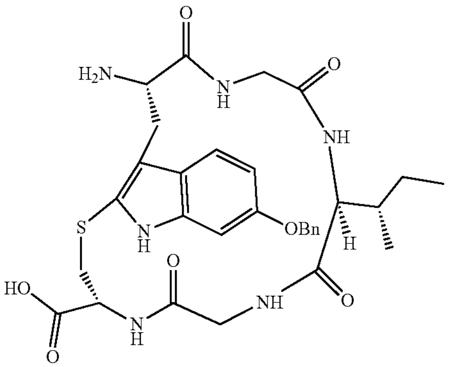

Monocyclic Pentapeptide 53 (125 mg, 0.17 mmol, 1.00 eq.) was stirred in TFA/DCM/TIPS (8:1.5:0.5) for 2 h at r.t. The solvent was removed under reduced pressure and the crude product was purified by C18 reverse phase chromatography (AcN/$H_2O$ 20% to 100%) to afford the fully deprotected monocyclic pentapeptide 55 as a white powder (100 mg, quant.).

HRMS (ESI): m/z calc. for $C_{31}H_{38}N_6O_7S$ $(M+H)^+$ 639.2595, found 639.2590.

Fully Deprotected Monocyclic Pentapeptide 56

55

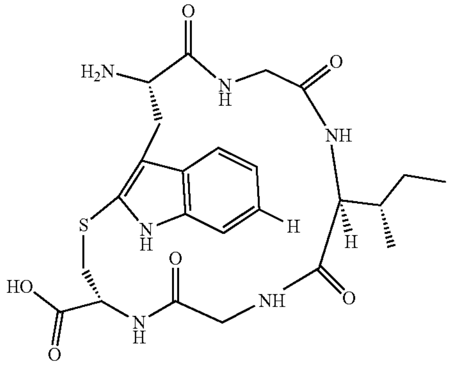

Monocyclic Pentapeptide 54 (250 mg, 0.34 mmol, 1.00 eq.) was stirred in TFA/DCM/TIPS (8:1.5:0.5) for 2 h at r.t. The solvent was removed under reduced pressure and the crude product was purified by C18 reverse phase chromatography (AcN/$H_2O$ 10% to 30%) to afford the fully deprotected monocyclic pentapeptide 56 as a white powder (200 mg, quant.).

HRMS (ESI): m/z calc. for $C_{24}H_{32}N_6O_6S$ $(M+H)^+$ 533.2177, found 533.2188.

Monocyclic Hexapeptide 67

67

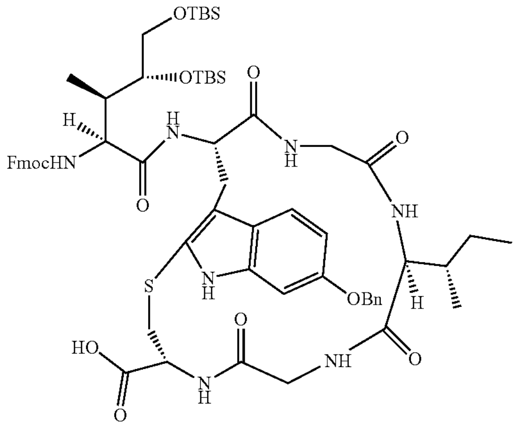

A solution of fully deprotected monocyclic pentapeptide 55 (42 mg, 0.66 mmol, 1.00 eq.) and MSA (11.6 μL, 0.723 mmol, 1.10 eq.) in DMA (2 mL) was stirred for 2 h at 50° C. Simultaneously, a solution of Fmoc-DHIle$(TBS)_2$—OH (13, 52 mg, 0.85 mmol, 1.30 eq.), COMU (36 mg, 0.85 mmol, 1.30 eq.) and DIPEA (15 μL, 0.85 mmol, 1.30 eq.) in DMA (0.4 mL) was stirred for 30 min at 0° C. The silylated monocyclic peptide was then added to the activated dihydroxyisoleucine derivative and stirred for 1 h at 0° C. then at r.t. overnight. Afterwards, the mixture was diluted with EtOAc (50 mL) and washed with 10% $KHSO_4$ solution (3×5 mL). The organic phase was washed with brine (2×20 mL), dried over $NaSO_4$ and evaporated under reduced pressure. The crude product of 67 was used in the next step without any further purification.

HRMS (ESI): m/z calc. for $C_{54}H_{87}N_7O_{12}SSi_2$ $(M+H)^+$ 1234.5745, found 1234.5745.

Monocyclic Hexapeptide 68

68

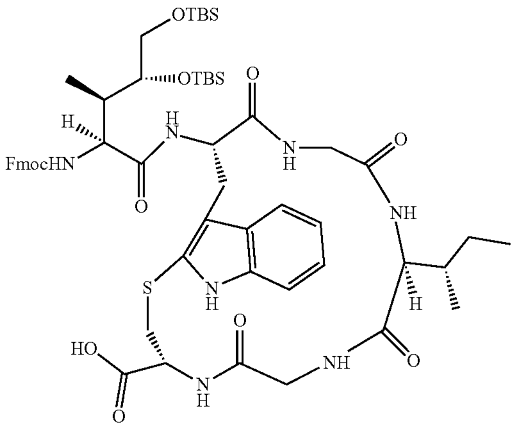

A solution of fully deprotected monocyclic pentapeptide 56 (100 mg, 0.188 mmol, 1.00 eq.) and MSA (33.2 μL, 0.207 mmol, 1.10 eq.) in DMA (4 mL) was stirred for 2 h at 50° C. Simultaneously, a solution of Fmoc-DHIle$(TBS)_2$—OH (13, 149 mg, 0.244 mmol, 1.30 eq.), COMU (104 mg, 0.244 mmol, 1.30 eq.) and DIPEA (42.5 μL, 0.244 mmol, 1.30 eq.) in DMA (1.25 mL) was stirred for 30 min at 0° C. The silylated monocyclic peptide was then added to the activated dihydroxyisoleucine derivative and stirred for 1 h at 0° C. then at r.t. overnight. Afterwards, the mixture was diluted with EtOAc (100 mL) and washed with 10% $KHSO_4$ solution (3×10 mL). The organic phase was washed with brine (2×25 mL), dried over $NaSO_4$ and evaporated under reduced pressure. The crude product of 68 was used in the next step without any further purification.

HRMS (ESI): m/z calc. for $C_{57}H_{31}N_7O_{11}SSi_2$ $(M+H)^+$ 1128.5326, found 1128.5316.

Synthesis of (9H-fluoren-9-yl)methyl (2S,4R)-4-hydroxypyrrolidine-2-carboxylate hydrochloride (2)

2

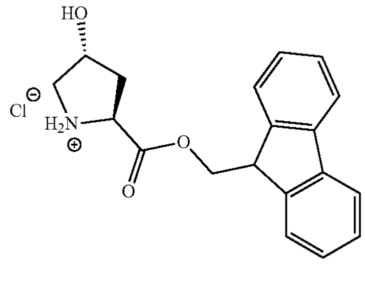

A solution of N-Boc-protected (2S,4R)-4-hydroxyproline 1 (5.0 g, 22 mmol, 1.0 eq.) in DMF (20 mL) was added dropwise to a solution of 9-fluorenemethanol (8.5 mg, 43 mmol, 2.0 eq.), EDC*HCl (8.3 g, 43 mmol, 2.0 eq.) and DMAP (396 mg, 3.24 mmol, 0.150 eq.) in DCM (220 mL). The reaction mixture was stirred at r.t. for 2 h. Then, 10% $KHSO_4$ solution (50 mL) was added. The organic phase was washed with brine (50 mL) and dried over $NaSO_4$. Afterwards, the solvent was removed under reduced pressure and the crude product was purified by column chromatography on silica gel (hexane/ethyl acetate=1:1) and treated with 4 m HCl in dioxane for 30 min. Evaporation of the solvent under reduced pressure afforded the product 2 as a white solid (3.7 g, 56%).

HRMS (ESI): m/z calc. for $C_{19}H_{19}NO_3$ $(M+H-HCl)^+$ 310.1438, found 310.1426.

Synthesis of (9H-fluoren-9-yl)methyl (2S,4R)-1-((S)-4-(allyloxy)-2-amino-4-oxobutanoyl)-4-hydroxypyrrolidine-2-carboxylate (3)

3

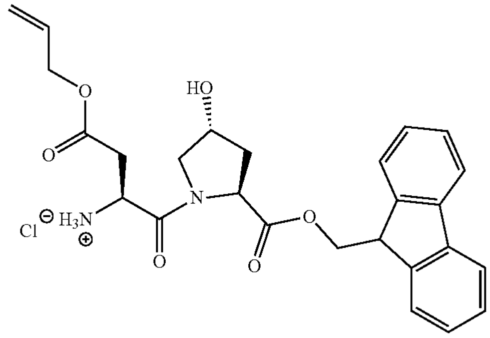

Boc-I-aspartic acid 4-allyl ester (287 mg, 1.05 mmol, 1.30 eq.), compound 2 (250 mg, 0.808 mmol, 1.0 eq.) and HATU (614 mg, 1.62 mmol, 2.0 eq.) were dissolved in DMF (2 mL) at 0° C. Then, DIPEA (563 μL, 3.23 mmol, 4 eq.) was added and reaction mixture was stirred at r.t. for 2 h. Subsequently, the reaction mixture was diluted with EtOAc (50 mL). The organic phase was washed with 10% $KHSO_4$ solution (2×10 mL), sat. $NaHCO_3$ (10 mL) and brine (10 mL). After drying over $NaSO_4$ and removal of the solvent under reduced pressure the crude product was purified by column chromatography on silica gel (hexane/ethyl acetate=2:1) and treated with 4 m HCl in dioxane for 30 min afterwards. Evaporation of the solvent under reduced pressure afforded the product 3 as a yellow oil (344 mg, 85%).

HRMS (ESI): m/z calc. for $C_{26}H_{28}N_2O_6$ (M+H−HCl)+ 465.2020, found 465.2017.

Synthesis of Monocyclic Octapeptide 5

5

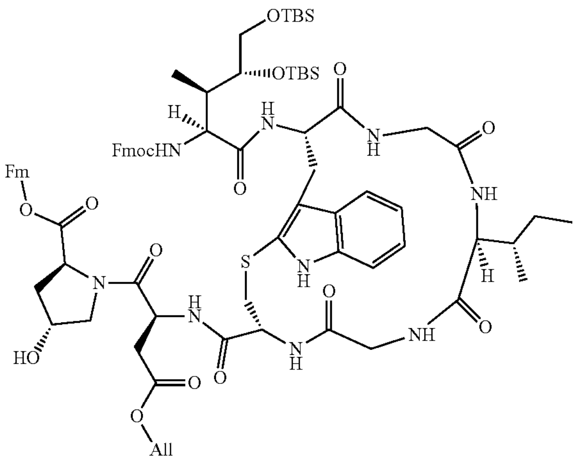

Fully deprotected monocyclic pentapeptide 4 (50 mg, 0.09 mmol, 1.00 eq.) was dissolved in DMA (1 mL) and MSA (17 μL, 0.1 mmol, 1.1 eq.) was added. The solution was stirred for 2 h at 50° C. A solution of Fmoc-Dhl(OTBS)$_2$—OH (75 mg, 0.12 mmol, 1.3 eq.), COMU (52 mg, 0.12 mmol, 1.3 eq.) and DIPEA (43 μL, 0.24 mmol, 2.6 eq.) in DMA (0.5 mL) was stirred for 30 min at 0° C. The silylated monocyclic pentapeptide was added to the preactivated amino acid and stirred for 1 h. Then, H-Asp(OAll)-Hyp-OFm*HCl (70 mg, 0.14 mmol, 1.5 eq.) and HATU (53 mg, 0.14 mmol, 1.5 eq) were added to the reaction mixture at 0° C. DIPEA (49 μL, 0.28 mmol, 3.0 eq.) was added and the reaction mixture was stirred for 2 h, then diluted with EtOAc (50 mL) and washed with 10% citric acid (2×10 mL) and sat. $NaHCO_3$ (2×10 mL). The organic phase was washed with brine (2×20 mL), dried over $NaSO_4$ and evaporated under reduced pressure. The crude product 5 was submitted to the next step without any further purification.

HRMS (ESI): m/z calc. for $C_{83}H_{107}N_9O_{16}SSi_2$ $(M+H)^+$ 1574.7167, found 1574.7134.

Synthesis of Monocyclic C- and N-Terminally Deprotected Octapeptide 6

6

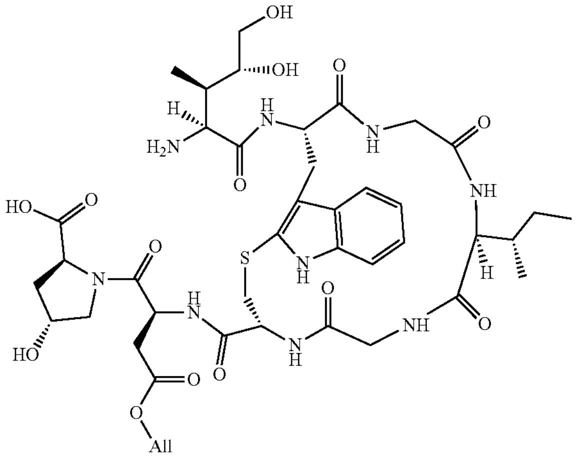

Monocyclic octapeptide 5 which was obtained from above reaction without further chromatographic purification step, was dissolved in DMF/ACN (2 mL). Then $Et_2NH$ (191 μL, 1.85 mmol, 20.0 eq.) was added and stirred for 30 min at r.t. The solvent was removed under reduced pressure and the precipitate was redissolved in THF (1 mL). Then, a solution of TBAF in THF (1 m, 0.85 mL, 10 eq) was added and the reaction mixture was stirred for 4 h at r.t. The solvent was evaporated in vacuo and the crude product purified by C18 reverse phase chromatography (AcN/$H_2O$ 5% to 70%) to afford the product 6 as a white solid (51 mg, 64% after four steps).

HRMS (ESI): m/z calc. for $C_{42}H_{59}N_9O_{14}S$ $(M+H)^+$ 946.3975, found 946.3972.

Synthesis of Allylester-Protected Deoxyamanin-Precursor (7)

7

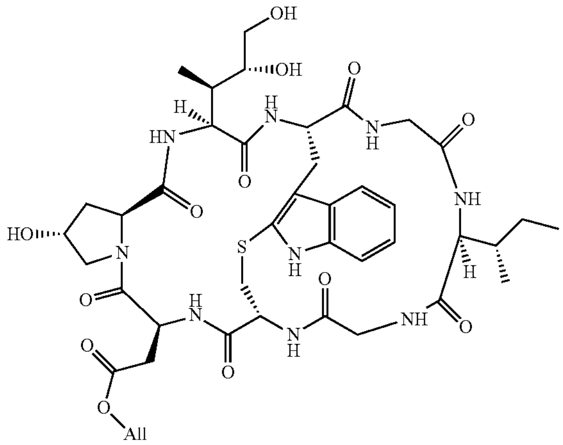

Monocyclic octapeptide 6 (10.0 mg, 10.6 μmol, 1.00 eq.) was dissolved in DMF (5 mL). Then, DIPEA (3.68 μL, 21.4 μmol, 2.00 eq.) and HATU (8.04 mg, 21.1 μmol, 2.00 eq) were added at 0° C. The reaction mixture was stirred for 5 h during which it was allowed to warm to r.t. The crude product was purified using preparative HPLC (Sunfire Prep C18 OBD 10 μm, 50×150 mm column, gradient A) to afford ally/protected Deoxyamanin-precursor 7 (6 mg, 68%) as a white powder.

HRMS (ESI): m/z calc. for $C_{42}H_{57}N_9O_{13}S$ $(M+H)^+$ 928.3869, found 928.3885.

Synthesis of (S)-Deoxyamanin (8)

8

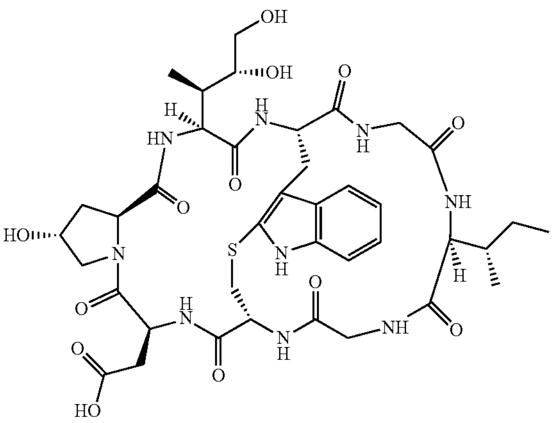

Deoxyamanin precursor 7 (3.0 mg, 3.2 μmol, 1.0 eq.) was dissolved in THF (0.3 mL). Then, morpholine (5.58 μL, 64.6 μmol, 20.0 eq.) and $Pd(PPh_3)_4$ (747 μg, 0.64 μmol, 0.2 eq) were added. The reaction mixture was stirred vigorously for 3 h. The crude product was purified using preparative HPLC (Sunfire Prep C18 OBD 10 μm, 50×150 mm column, gradient B) to afford (S)-Deoxyamanin (8) (1.5 mg, 50%) as a white powder.

HRMS (ESI): m/z calc. for $C_{39}H_{53}N_9O_{13}S$ $(M+H)^+$ 888.3556, found 888.3529.

Preparative HPLC Purification Gradients:

Gradient A:

0-30 min 10%-30% B, 30-35 min 30-100% B; 40-45 min 100% B; 45-50 min, 100-10% B 0.1% formic acid in water (Solvent A) and 0.1% formic acid in ACN (Solvent B).

Gradient B:

0-30 min 15%-40% B, 30-35 min 40-100% B; 35-40 min 100% B, 40-15 min 15% B 0.1% formic acid in water (Solvent A) and 0.1% formic acid in ACN (Solvent B).

The invention claimed is:

1. A method for preparation of a compound of formula (I)

(I)

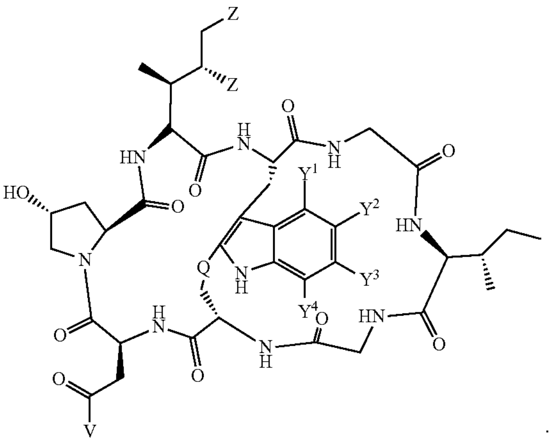

.

wherein, a) a compound of formula (IIa)

(IIa)

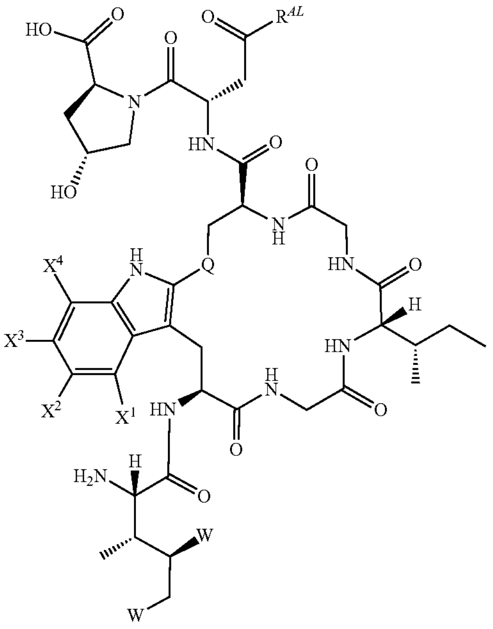

is reacted with a peptide bond forming reagent in a reaction step (a), and where applicable, the compound is reacted with a deprotection agent removing $R^{PGP}$ and/or $R^{PGOH}$ and/or $R^{AL}$ and/or $R^{AMIN}$, or wherein, a compound of formula (IIb)

(IIb)

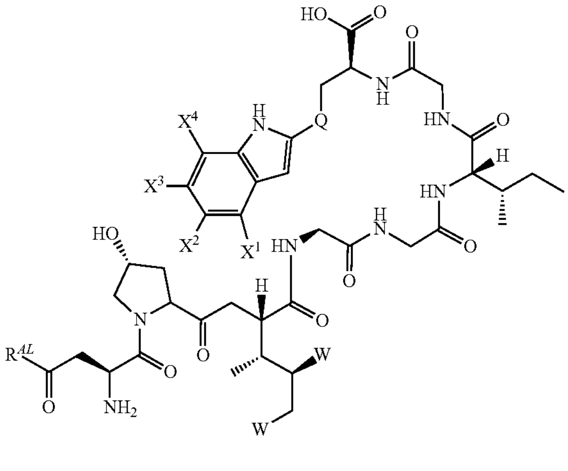

is reacted with a peptide bond forming reagent in reaction step (b), and where applicable, the compound is reacted with a deprotection agent removing $R^{PGP}$ and/or $R^{PGOH}$ and/or $R^{AL}$ and/or $R^{AMIN}$, or wherein, b) a compound of formula (IIc)

(IIc)

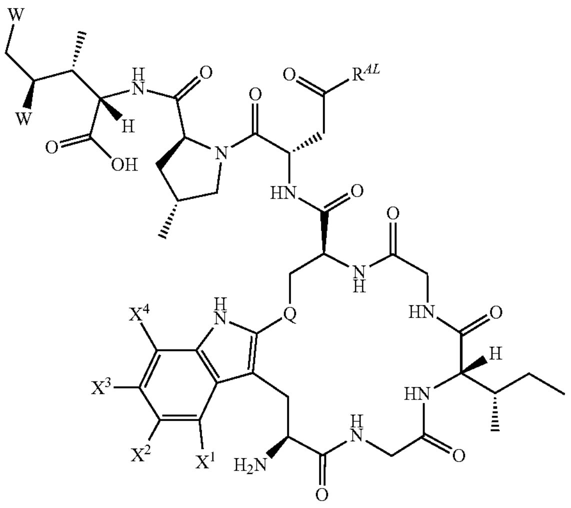

is reacted with a peptide bond forming reagent in a reaction step (c), and where applicable, the compound is reacted with a deprotection agent removing $R^{PGP}$ and/or $R^{PGOH}$ and/or $R^{AL}$ and/or $R^{AMIN}$, or wherein, a compound of formula (IId)

(IId)

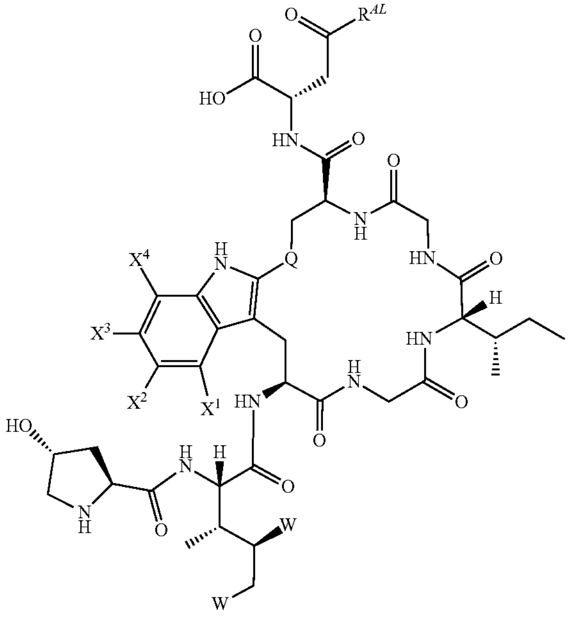

is reacted with a peptide bond forming reagent in a reaction step (d), and where applicable, the compound is reacted with a deprotection agent removing $R^{PGP}$ and/or $R^{PGOH}$ and/or $R^{AL}$ and/or $R^{AMIN}$ wherein, $X^1$, $X^2$, $X^3$, and $X^4$, and $Y^1$, $Y^2$, $Y^3$, and $Y^4$ are H, or one, two, three or all of $Y^1$, $Y^2$, $Y^3$, and $Y^4$ are OH or $NH_2$ and all other Y are H and the corresponding X is $NHR^{AMIN}$ or $OR^{PGP}$ and all other X are H, wherein $R^{PGP}$ is a protecting group for phenolic OH groups, or $R^{AMIN}$ is a protecting group for phenolic amino groups, or one, two, three or all of $Y^1$, $Y^2$, $Y^3$, and $Y^4$ and the corresponding X are selected from F, Cl, Br, I, CN, $NO_2$, acyl, $N_3$, or alkyne, and all other X and Y are H, Z and W are H, or Z is OH and W is $OR^{PGOH}$, wherein $R^{PGOH}$ is a protecting group for hydroxyl groups, $R^{AL}$ is a protected carboxyl-group or a 1-5AA peptide, V is OH or a 1-5AA peptide, and Q is S or SO.

2. The method of claim 1, wherein a compound of formula (III)

(III)

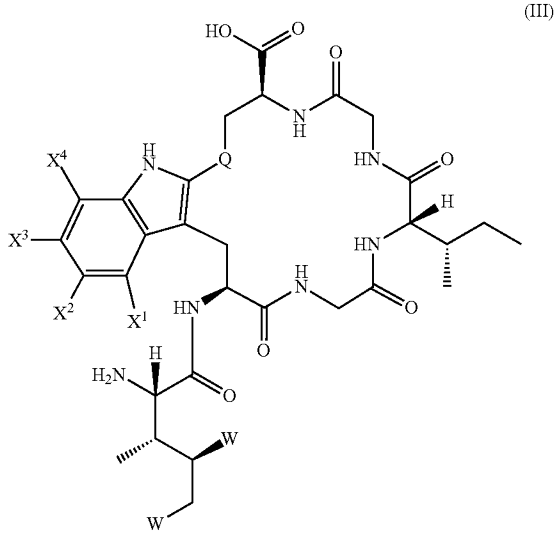

and a compound of formula (IV)

(IV)

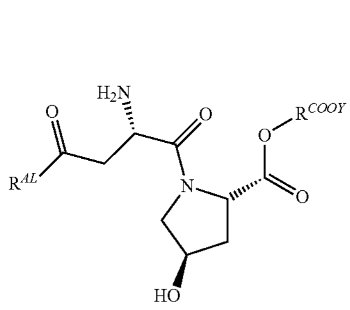

wherein, $R^{COOY}$ is a carboxyl-protecting group, wherein (III) and (IV) are reacted with a peptide bond forming reagent in a reaction step (e) to yield the compound of formula (IIa).

3. The method of claim 2, wherein a compound of formula (V)

(V)

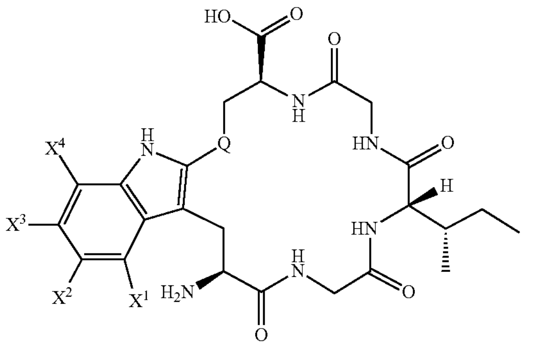

and a compound of formula (VI)

(VI)

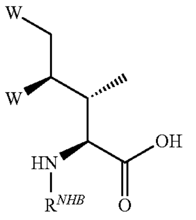

wherein, $R^{NHB}$ is an amino protecting group, and wherein the amino-group of (V) is preactivated with N-trimethylsilyl amine, and preactivated (V) and (VI) are reacted with a peptide bond forming reagent in a reaction step (f) to yield the compound (III).

4. The method of claim 1, wherein a compound of formula (V)

(V)

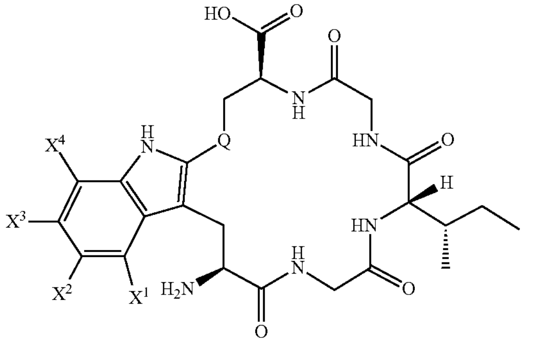

and a compound of formula (VII)

(V)

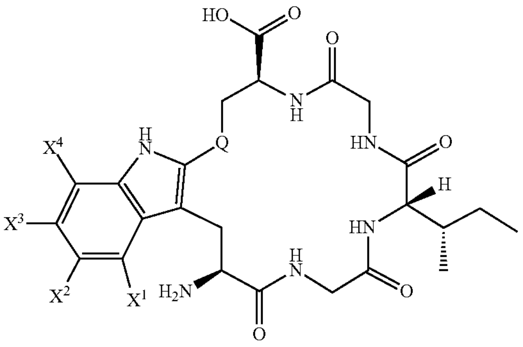

wherein, $R^{NHB}$ is an amino protecting group, and wherein, the amino-group of (V) is preactivated with N-trimethylsilyl amine, and preactivated (V) and (VII) are reacted with a peptide bond forming reagent, or the amino-group of (V) is preactivated with N-trimethylsilyl amine, and the carboxyl-group of compound (VII) is preactivated with an activating group selected from the group consisting of O-PFP-ester, O-PCP-ester, and OSu-ester, and preactivated (V) and preactivated (VII) are reacted, in a reaction step (g) to yield the compound (IIb).

5. The method of claim 1, wherein for a compound of formula (Idesox)

(Idesox)

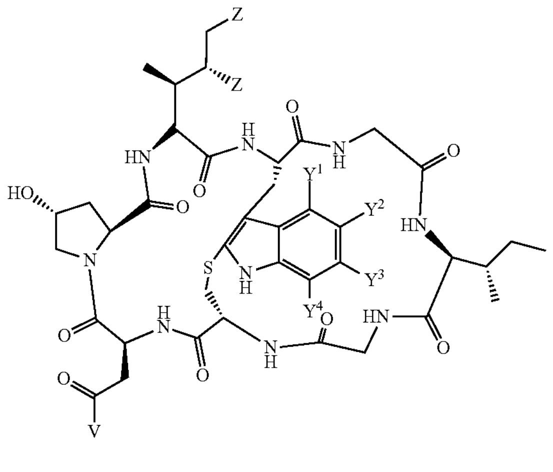

wherein, the sulfur atom is oxidized in a reaction step (h) to yield the compound (Iox)

(Iox)

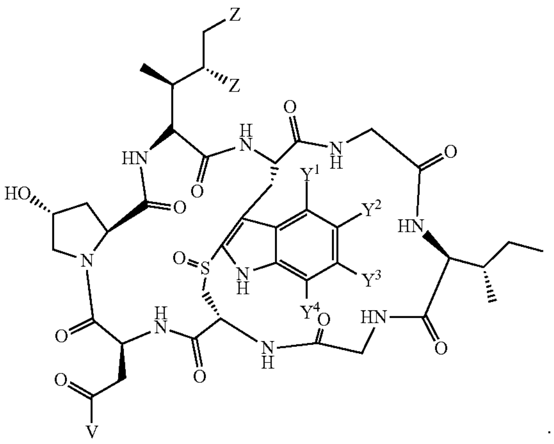

6. The method of claim 3, wherein for a compound of formula (Vdesox)

(Vdesox)

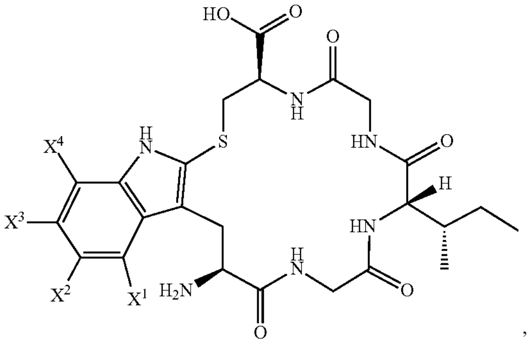

the sulfur atom is oxidized in a reaction step (i) to yield the compound (Vox)

(Vox)

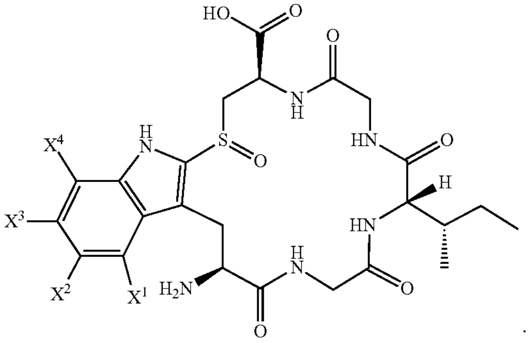

7. The method of claim 3, wherein a compound of formula (VIII)

(VIII)

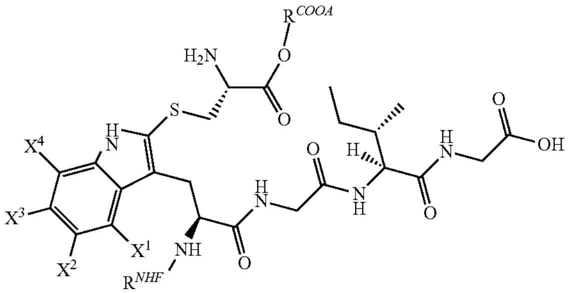

wherein, $R^N$HF is an amino protecting group, and $R^{COOA}$ is a carboxyl-protecting group, is reacted with a peptide bond forming reagent, in a reaction step (j), and the compound is reacted with a deprotection agent removing $R^N$HF and $R^{COOA}$ in a reaction step (k), to yield the compound of formula (Vdesox) or (V).

8. The method of claim 7, wherein a compound of formula (IX)

(IX)

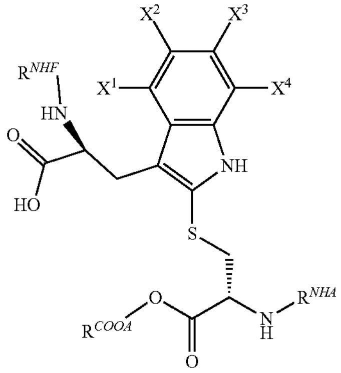

and a compound of formula (X)

(X)

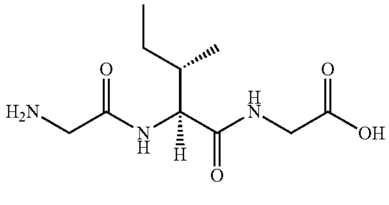

wherein, $R^N$HA is an amino protecting group, and wherein compound (VII) is preactivated with a peptide bond forming reagent, followed by a reaction with the silylated compound (VIII), or preactivated as in OSu-ester, followed by a reaction with the compound (VII) in a reaction step (l), and the compound is reacted with a deprotection agent removing $R^{NHA}$ in a reaction step (m), to yield the compound of formula (VIII).

9. The method of claim 8, wherein a compound of formula (XI)

(XI)

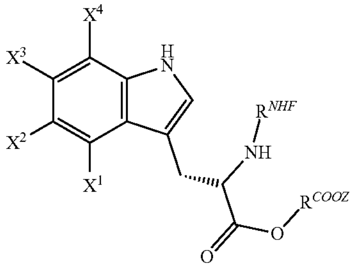

and a compound of formula (XII)

(XII)

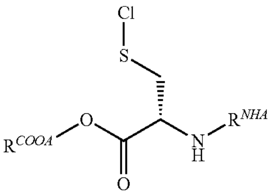

wherein, $R^{COOZ}$ is a carboxyl-protecting group, or $R^{COOZ}$ is H, are reacted in a reaction step (n), and if $R^{COOZ}$ is a carboxyl-protecting group, the compound is reacted with a deprotection agent removing $R^{COOZ}$ in a reaction step (o), to yield the compound of formula (IX).

10. The method of claim 4, wherein a compound of formula (VI)

(VI)

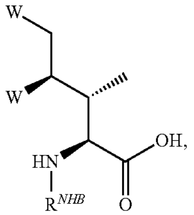

a compound of formula (XIII)

(XIII)

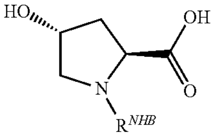

and a compound of formula (XIV)

(XIV)

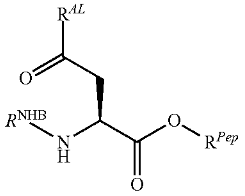

wherein, $R^{Pep}$ is an active ester, are reacted with solid phase peptide synthesis in a reaction step (p), to yield the compound of formula (VII).

11. The method of claim 1, wherein the compound of formula (IIa)

(IIa)

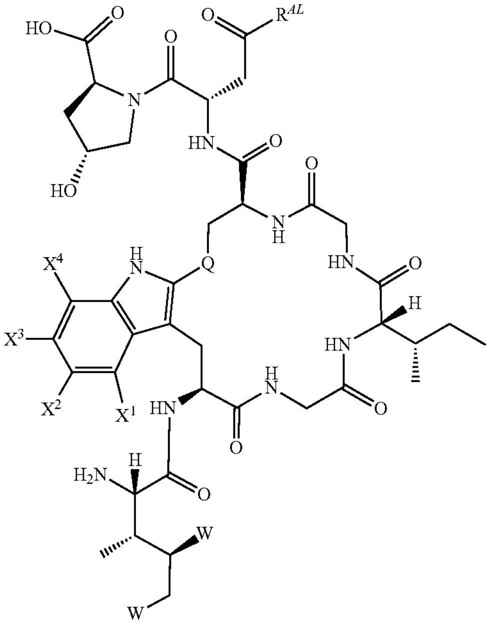

is reacted with a peptide bond forming reagent in a reaction step (a), and where applicable, the compound is reacted with a deprotection agent removing $R^{PGP}$ and/or $R^{PGOH}$ and/or $R^{AL}$ and/or $R^{AMIN}$;

wherein, $X^1$, $X^2$, $X^3$, and $X^4$, and $Y^1$, $Y^2$, $Y^3$, and $Y^4$ are H, or one, two, three or all of $Y^1$, $Y^2$, $Y^3$, and $Y^4$ are OH or $NH_2$ and all other Y are H and the corresponding X is $NHR^{AMIN}$ or $OR^{PGP}$ and all other X are H, wherein $R^{PGP}$ is a protecting group for phenolic OH groups, or $R^{AMIN}$ is a protecting group for phenolic amino groups, or one, two, three or all of $Y^1$, $Y^2$, $Y^3$, and $Y^4$ and the corresponding X are selected a from F, Cl, Br, I, CN, $NO_2$, acyl, $N_3$, or alkyne, and all other X and Y are H, Z and W are H, or Z is OH and W is $OR^{PGOH}$, wherein $R^{PGOH}$ is a protecting group for hydroxyl groups, $R^{AL}$ is a protected carboxyl-group or a 1-5AA peptide, V is OH or a 1-5AA peptide, and Q is S or SO.

12. The method of claim 2, wherein a compound of formula (III)

(III)

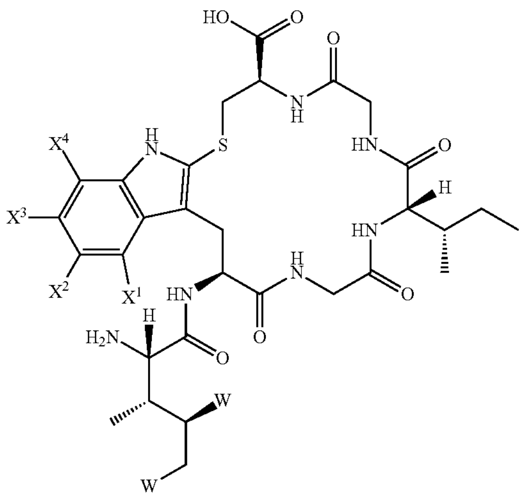

and a compound of formula (IV)

(IV)

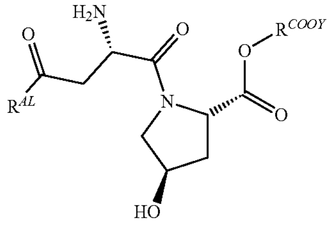

wherein, $R^{COOY}$ is a carboxyl-protecting group selected from the group consisting of fluorenylmethyl and benzyl, wherein (III) and (IV) are reacted with a peptide bond forming reagent selected from the group consisting of HATU, COMU, HBTU, TBTU, TOMBU, COMBU, and HCTU, in a reaction step (e) to yield the compound of formula (IIa).

13. The method of claim 12, wherein a compound of formula (V)

(V)

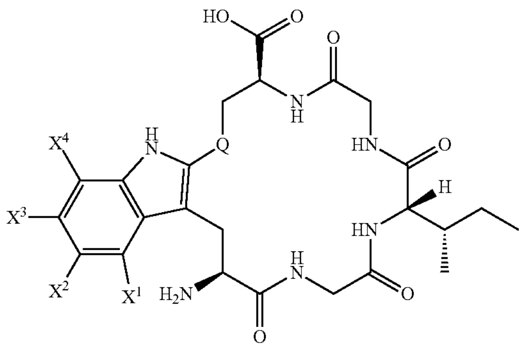

and a compound of formula (VI)

(VI)

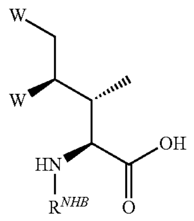

wherein, $R^{NHB}$ is an amino protecting group, wherein, the amino-group of (V) is preactivated with N-trimethylsilyl amine, and preactivated (V) and (VI) are reacted with a peptide bond forming reagent selected from a group consisting of HATU, COMU, HBTU, TBTU, TOMBU, COMBU, and HCTU, in a reaction step (f) to yield the compound (III).

14. The method of claim 1, wherein the compound of formula (I) is (Idesox)

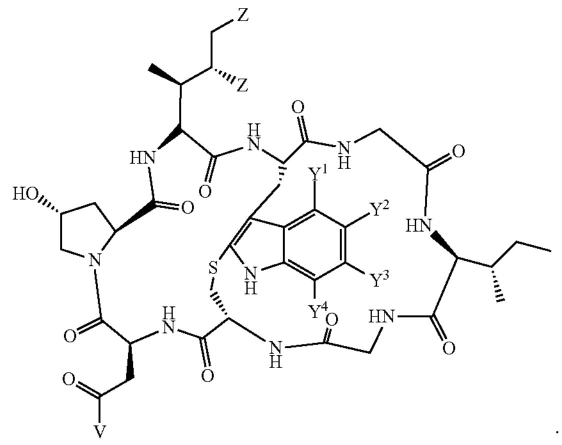

.

15. The method of claim 1, wherein the compound of formula (I) is

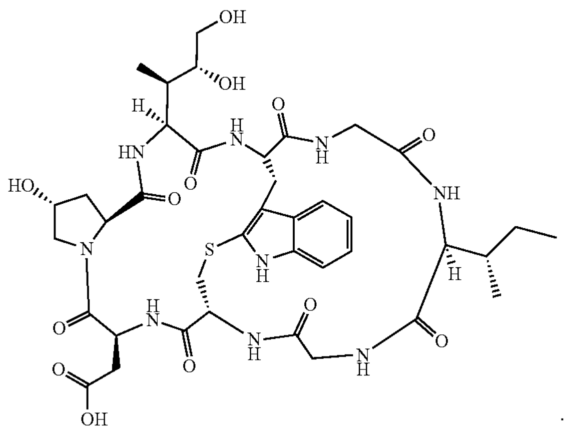

.

16. The method of claim 13, wherein the $R^{NHB}$ is an amino protecting group cleavable under alkaline conditions.

17. The method of claim 16, wherein the $R^{NHB}$ is Fmoc.

* * * * *